(12) United States Patent
Kato et al.

(10) Patent No.: US 10,159,450 B2
(45) Date of Patent: Dec. 25, 2018

(54) X-RAY CT APPARATUS INCLUDING A PHOTON-COUNTING DETECTOR, AND AN IMAGE PROCESSING APPARATUS AND AN IMAGE PROCESSING METHOD FOR CORRECTING DETECTION SIGNALS DETECTED BY THE PHOTON-COUNTING DETECTOR

(71) Applicant: TOSHIBA MEDICAL SYSTEMS CORPORATION, Otawara-Shi (JP)

(72) Inventors: Tooru Kato, Nasushiobara (JP); Hiroaki Nakai, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 392 days.

(21) Appl. No.: 14/872,478

(22) Filed: Oct. 1, 2015

(65) Prior Publication Data
US 2016/0095564 A1    Apr. 7, 2016

(30) Foreign Application Priority Data

Oct. 1, 2014   (JP) .................... 2014-203203
Sep. 30, 2015  (JP) .................... 2015-193931

(51) Int. Cl.
*A61B 6/03*    (2006.01)
*A61B 6/00*    (2006.01)

(52) U.S. Cl.
CPC ............ *A61B 6/4241* (2013.01); *A61B 6/032* (2013.01); *A61B 6/4208* (2013.01); *A61B 6/4233* (2013.01); *A61B 6/52* (2013.01)

(58) Field of Classification Search
CPC ..... A61B 6/032; A61B 6/4208; A61B 6/4233; A61B 6/4241; A61B 6/52
(Continued)

(56) References Cited

U.S. PATENT DOCUMENTS 7,263,167 B2 *  8/2007  Walter .................. A61B 6/032
                                              378/116
7,480,362 B2 *  1/2009  Carmi .................. A61B 6/032
                                              378/19
(Continued)

FOREIGN PATENT DOCUMENTS

JP      11-109040 A      4/1999
JP    2004-325183 A    11/2004
(Continued)

OTHER PUBLICATIONS

Hideki Kato, et al., "Energy-Absorption Response of Cadmium Zinc Telluride (CdZnTe) Semiconductor Detectors to X-ray Photon Beams" T. IEE Japan, vol. 120-C, No. 12, 2000, pp. 1774-1780.

*Primary Examiner* — Allen C. Ho
(74) *Attorney, Agent, or Firm* — Oblon, McClelland, Maier & Neustadt, L.L.P.

(57) ABSTRACT

An X-ray computed tomography (CT) apparatus according to an embodiment includes a photon-counting detector, correction circuitry, and reconstruction circuitry. The photon-counting detector includes a plurality of X-ray detection elements detecting X-ray photons applied from an X-ray tube. The correction circuitry corrects detection signals detected by the photon-counting detector for the respective X-ray detection elements, based on a centroid of an X-ray spectrum detected by the photon-counting detector. The reconstruction circuitry reconstructs a CT image based on the corrected detection signals.

14 Claims, 19 Drawing Sheets

(58) Field of Classification Search
USPC .................. 378/19, 98.8, 207; 250/370.09
See application file for complete search history.

(56) References Cited

U.S. PATENT DOCUMENTS

| | | | | |
|---|---|---|---|---|
| 7,492,967 | B2* | 2/2009 | Toki | A61B 6/032 |
| | | | | 382/299 |
| 7,696,483 | B2* | 4/2010 | Tkaczyk | G01T 1/171 |
| | | | | 250/370.06 |
| 7,894,576 | B2* | 2/2011 | Carmi | G01T 1/2985 |
| | | | | 250/370.09 |
| 8,213,566 | B2* | 7/2012 | Roessl | A61B 5/4869 |
| | | | | 378/5 |
| 8,243,874 | B2* | 8/2012 | Carmi | G01T 1/2985 |
| | | | | 250/366 |
| 8,338,791 | B2* | 12/2012 | Proksa | G01T 1/171 |
| | | | | 250/369 |
| 8,350,221 | B2* | 1/2013 | Steadman Booker | G01T 1/17 |
| | | | | 250/336.1 |
| 8,373,135 | B2* | 2/2013 | Kappler | G01T 1/247 |
| | | | | 250/336.1 |
| 8,378,310 | B2* | 2/2013 | Bornefalk | G06T 11/005 |
| | | | | 250/370.01 |
| 8,422,636 | B2* | 4/2013 | Greenberg | G01T 1/29 |
| | | | | 378/207 |
| 8,450,695 | B2* | 5/2013 | Kappler | G01T 1/17 |
| | | | | 250/370.09 |
| 8,488,854 | B2* | 7/2013 | Arenson | G06T 11/005 |
| | | | | 378/1 |
| 8,493,483 | B2* | 7/2013 | Nishihara | H04N 5/32 |
| | | | | 348/294 |
| 8,618,471 | B2* | 12/2013 | Steadman | G01T 1/17 |
| | | | | 250/252.1 |
| 8,653,471 | B2* | 2/2014 | Proksa | A61B 6/032 |
| | | | | 250/363.01 |
| 8,716,652 | B2* | 5/2014 | Hannemann | G01T 1/17 |
| | | | | 250/252.1 |
| 8,891,845 | B2* | 11/2014 | Ogawa | A61B 6/14 |
| | | | | 382/128 |
| 8,913,711 | B2* | 12/2014 | Moriyasu | A61B 6/03 |
| | | | | 378/4 |
| 8,941,076 | B2* | 1/2015 | Abraham | G01T 1/171 |
| | | | | 250/336.1 |
| 8,988,267 | B1* | 3/2015 | Kimura | G01T 1/2928 |
| | | | | 341/155 |
| 9,000,385 | B2* | 4/2015 | Dror | G01T 1/171 |
| | | | | 250/370.06 |
| 9,020,092 | B2* | 4/2015 | Wang | A61B 6/583 |
| | | | | 378/5 |
| 9,052,266 | B2* | 6/2015 | Miyazaki | A61B 6/4241 |
| 9,075,147 | B2* | 7/2015 | Schroter | G01T 1/247 |
| 9,084,542 | B2* | 7/2015 | Bouhnik | A61B 6/032 |
| 9,109,953 | B2* | 8/2015 | Sasaki | G01J 1/44 |
| 9,160,939 | B2* | 10/2015 | Funaki | H03M 1/145 |
| 9,207,332 | B2* | 12/2015 | Spahn | G01T 1/17 |
| 9,216,302 | B2* | 12/2015 | Kuwahara | A61N 5/1039 |
| 9,220,469 | B2* | 12/2015 | Jin | A61B 6/4241 |
| 9,256,938 | B2* | 2/2016 | Petschke | G06T 7/0012 |
| 9,268,035 | B2* | 2/2016 | Herrmann | G01T 1/17 |
| 9,291,724 | B2* | 3/2016 | Proksa | G01T 1/24 |
| 9,292,946 | B2* | 3/2016 | Zou | G06T 11/006 |
| 9,294,700 | B2* | 3/2016 | Nishihara | H01L 27/14603 |
| 9,301,378 | B2* | 3/2016 | Steadman Booker | G01T 1/24 |
| 9,310,490 | B2* | 4/2016 | Abraham | G01T 1/17 |
| 9,344,661 | B2* | 5/2016 | Saito | G01T 1/208 |
| 9,351,701 | B2* | 5/2016 | Yamakawa | A61B 6/025 |
| 9,354,331 | B2* | 5/2016 | Sagoh | A61B 6/032 |
| 9,414,797 | B2* | 8/2016 | Flohr | A61B 6/032 |
| 9,417,339 | B2* | 8/2016 | Spahn | G01T 1/247 |
| 9,423,515 | B2* | 8/2016 | Roessl | G01T 1/241 |
| 9,444,344 | B2* | 9/2016 | Kim | G01T 1/247 |
| 9,456,790 | B2* | 10/2016 | Taguchi | A61B 6/4241 |
| 9,459,358 | B2* | 10/2016 | Wang | G01T 7/005 |
| 9,504,438 | B2* | 11/2016 | Proksa | G01T 1/24 |
| 9,517,045 | B2* | 12/2016 | Kang | G01N 23/087 |
| 9,528,947 | B2* | 12/2016 | Kang | G01N 23/04 |
| 9,532,759 | B2* | 1/2017 | Taguchi | A61B 6/032 |
| 9,535,172 | B2* | 1/2017 | Lee | G01T 1/24 |
| 9,535,175 | B2* | 1/2017 | Laurence | G01T 1/1647 |
| 9,547,090 | B2* | 1/2017 | Matsuda | G01T 1/2985 |
| 9,579,075 | B2* | 2/2017 | Besson | G01T 1/2985 |
| 9,595,101 | B2* | 3/2017 | Kato | G06T 11/005 |
| 9,602,745 | B2* | 3/2017 | Nishihara | H04N 5/378 |
| 9,610,055 | B2* | 4/2017 | Taguchi | A61B 6/5205 |
| 9,645,260 | B2* | 5/2017 | Abraham | G01T 1/247 |
| 9,662,077 | B2* | 5/2017 | Moriyasu | A61B 6/4241 |
| 9,664,798 | B2* | 5/2017 | Kappler | G01T 1/17 |
| 9,678,220 | B2* | 6/2017 | Herrmann | G01T 1/17 |
| 9,687,207 | B2* | 6/2017 | Zou | A61B 6/585 |
| 9,693,743 | B2* | 7/2017 | Arakita | G01T 1/1606 |
| 9,746,566 | B2* | 8/2017 | Herrmann | G01T 1/247 |
| 9,759,822 | B2* | 9/2017 | Daerr | G01T 1/17 |
| 9,778,379 | B2* | 10/2017 | Sagoh | G01T 1/208 |
| 9,795,353 | B2* | 10/2017 | Teshigawara | A61B 6/5205 |
| 9,801,595 | B2* | 10/2017 | Cao | A61B 6/4241 |
| 9,808,210 | B2* | 11/2017 | Yamazaki | A61B 6/032 |
| 9,836,859 | B2* | 12/2017 | Zou | G06T 11/003 |
| 9,841,389 | B2* | 12/2017 | Tamura | G01N 23/046 |
| 9,846,244 | B2* | 12/2017 | Abraham | G01T 1/17 |
| 9,867,590 | B2* | 1/2018 | Tamura | A61B 6/585 |
| 9,872,661 | B2* | 1/2018 | Ono | A61B 6/5205 |
| 9,895,128 | B2* | 2/2018 | Takahashi | A61B 6/5258 |
| 9,913,622 | B2* | 3/2018 | Ida | A61B 6/5205 |
| 9,924,916 | B2* | 3/2018 | Kato | A61B 6/4208 |
| 9,971,047 | B2* | 5/2018 | Tamura | G01T 1/2985 |

FOREIGN PATENT DOCUMENTS

| | | |
|---|---|---|
| JP | 2006-101926 A | 4/2006 |
| JP | 2011-85479 A | 4/2011 |
| JP | 2014-128456 A | 7/2014 |
| JP | 2016-19633 A | 2/2016 |
| WO | WO 2012/144589 A1 | 10/2012 |

\* cited by examiner

FIG.13
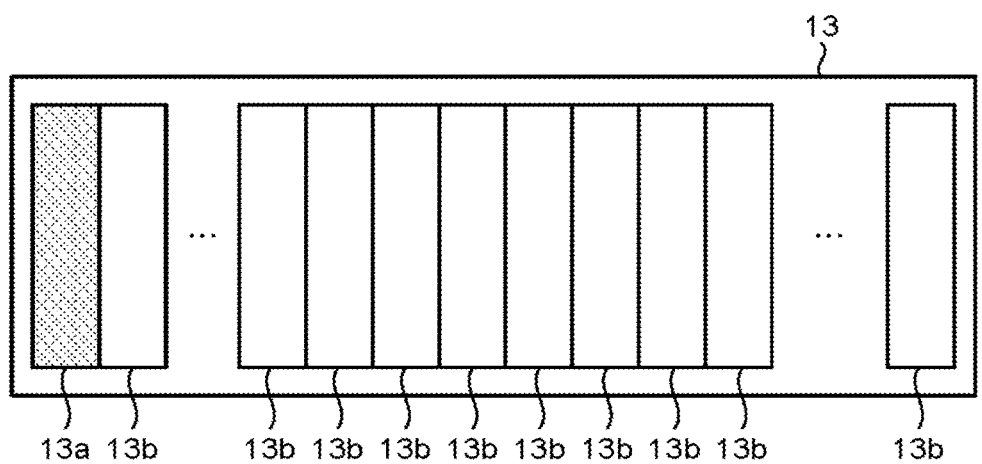
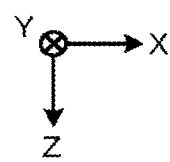

▨ REFERENCE DETECTION ELEMENT (HIGH ENERGY RESOLUTION)
☐ NORMAL X-RAY DETECTION ELEMENT
◨ NORMAL X-RAY DETECTION ELEMENT (BEING IRRADIATED WITH X-RAYS)

FIG.22
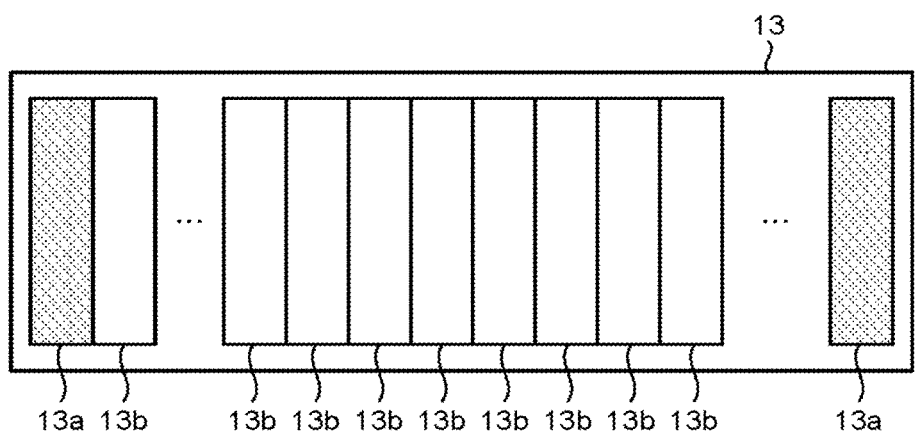
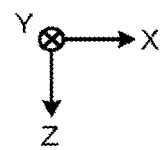
FIG.23
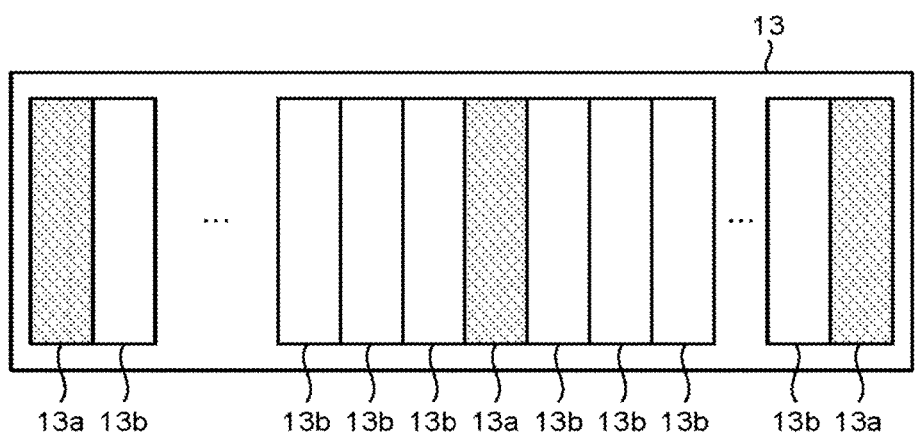
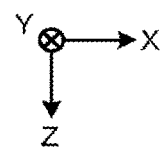

X-RAY CT APPARATUS INCLUDING A PHOTON-COUNTING DETECTOR, AND AN IMAGE PROCESSING APPARATUS AND AN IMAGE PROCESSING METHOD FOR CORRECTING DETECTION SIGNALS DETECTED BY THE PHOTON-COUNTING DETECTOR

CROSS-REFERENCE TO RELATED APPLICATIONS

This application is based upon and claims the benefit of priority from Japanese Patent Application No. 2014-203203, filed on Oct. 1, 2014; and Japanese Patent Application No. 2015-193931, filed on Sep. 30, 2015, the entire contents of all of which are incorporated herein by reference.

FIELD

Embodiments described herein relate generally to an X-ray computed tomography (CT) apparatus, an image processing apparatus, and an image processing method.

BACKGROUND

Nowadays, photon-counting X-ray detectors are known as X-ray detectors used in X-ray CT apparatuses. Each of X-ray detection elements included in a photon-counting X-ray detector outputs a detection signal that enables counting of incident X-ray photons, and enables measurement of an energy value (keV) of each of the X-ray photons. When a photon-counting detector is used, calibration is indispensable to correct variation in X-ray energy sensitivity between the X-ray detection elements.

BRIEF DESCRIPTION OF THE DRAWINGS

FIG. 13 is a diagram for explaining an example of a detector according to a second embodiment;
FIG. 22 is a diagram for explaining another example of the detector according to the second embodiment;
FIG. 23 is a diagram for explaining another example of the detector according to the second embodiment.

DETAILED DESCRIPTION

The following is explanation of an X-ray computed tomography (CT) apparatus, an image processing apparatus, and an image processing method according to embodiments with reference to drawings.

An X-ray CT apparatus explained in the following embodiments is an apparatus that is capable of executing photon counting CT. Specifically, the X-ray CT apparatus explained in the following embodiments is not a conventional integral (current mode measuring system) detector, but an apparatus that is capable of reconstructing X-ray CT image data with high SN ratio, by counting X-rays that are transmitted through a subject using a photon-counting detector.

The X-ray computed tomography (CT) apparatus according to the embodiments includes a photon-counting detector, correction circuitry, and reconstruction circuitry. The photon-counting detector includes a plurality of X-ray detection elements detecting X-ray photons applied from an X-ray tube. The correction circuitry corrects detection signals detected by the photon-counting detector for the respective X-ray detection elements, based on a centroid of an X-ray spectrum detected by the photon-counting detector. The reconstruction circuitry reconstructs a CT image based on the corrected detection signals.

First Embodiment

Figure 1:
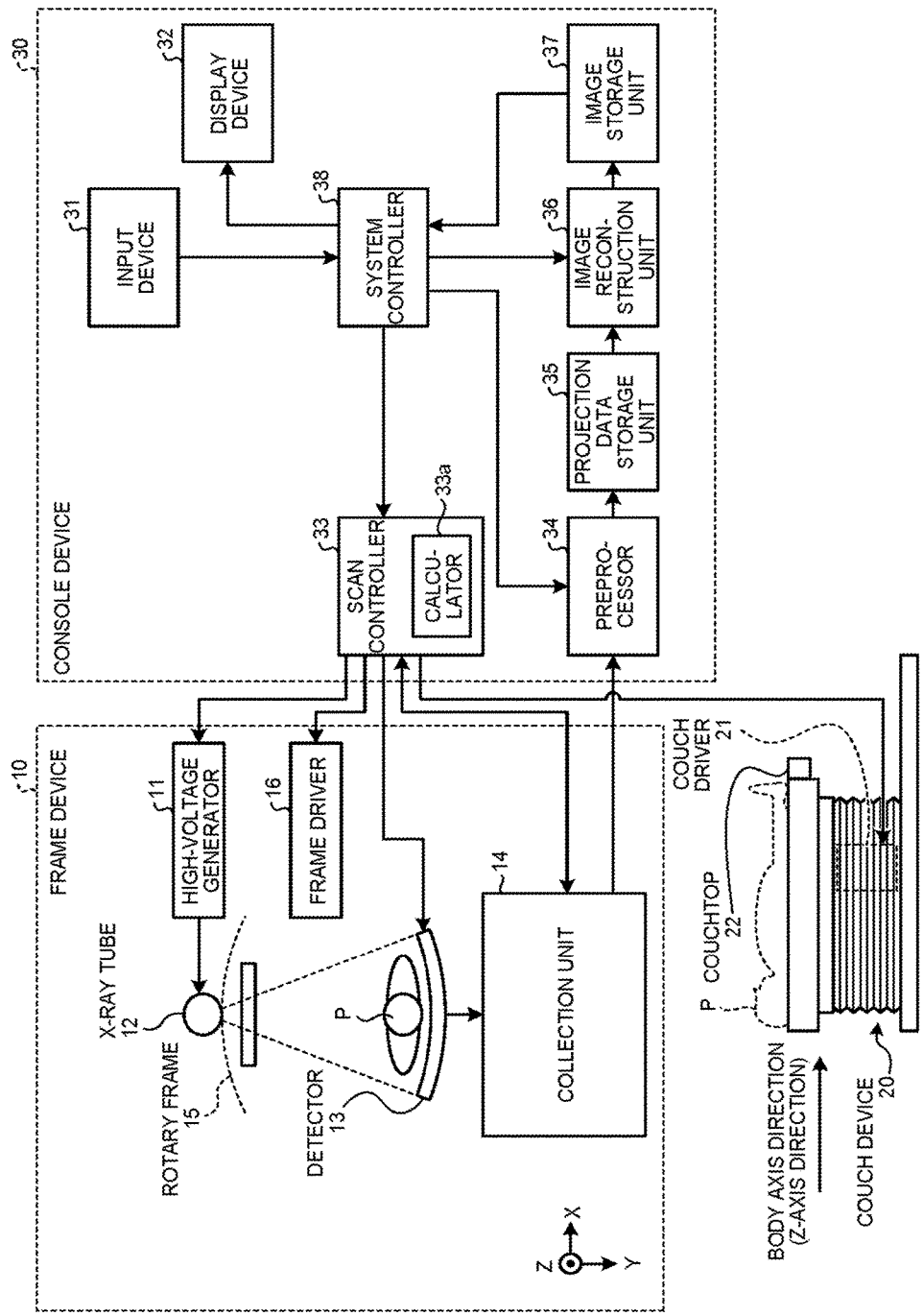
FIG. 1 is a diagram illustrating a configuration example of an X-ray CT apparatus according to a first embodiment.

FIG. 1 is a diagram illustrating a configuration example of an X-ray CT apparatus according to a first embodiment. As illustrated in FIG. 1, the X-ray CT apparatus according to the first embodiment includes a frame device 10, a couch device 20, and a console device 30.

Figure 2:
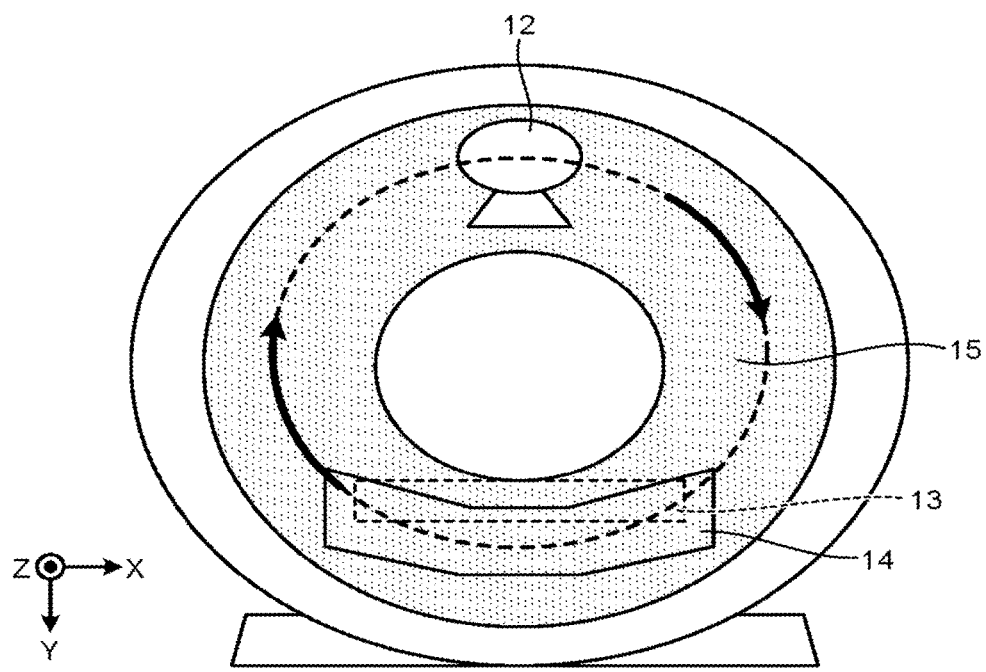
FIG. 2 is a front view of a frame device according to the first embodiment.

The frame device 10 is a device that applies X-rays to a subject P, to collect data related to X-rays that are transmitted through the subject P. The frame device 10 includes a high-voltage generator 11, an X-ray tube 12, a detector 13, a collection unit 14, a rotary frame 15, and a frame driver 16. FIG. 2 is a front view of the frame device 10 according to the first embodiment.

As illustrated in FIG. 2, the rotary frame 15 is an annular frame that supports the X-ray tube 12 and the detector 13 such that they are opposed to each other with the subject P interposed therebetween. The rotary frame 15 is rotated at high speed on a circular track by the frame driver 16, which is described later, with the subject P serving as the center.

The X-ray tube 12 is a vacuum tube that applies an X-ray beam to the subject P with high voltage supplied from the high-voltage generator 11 described later. The X-ray tube 12 applies an X-ray beam to the subject P along with the rotation of the rotary frame 15.

The high-voltage generator 11 is a device that supplies high voltage to the X-ray tube 12. The X-ray tube 12 generates X-rays using high voltage supplied from the high-voltage generator 11. Specifically, the high-voltage generator 11 regulates tube voltage and tube current supplied to the X-ray tube 12, to regulate the X-ray dose applied to the subject P.

The frame driver 16 rotates and drives the rotary frame 15, to revolve the X-ray tube 12 and the detector 13 along the circular track with the subject P serving as the center.

Figure 3:
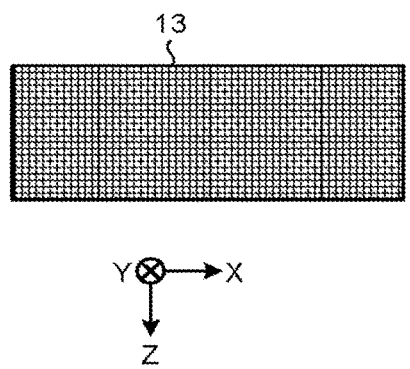
FIG. 3 is a diagram for explaining an example of a detector according to the first embodiment.

The detector 13 is a photon-counting detector, and includes a plurality of X-ray detection elements (also referred to as "sensors") to count light derived from X-rays that are transmitted through the subject P. As an example, the X-ray detection elements included in the detector 13 according to the first embodiment are indirect-conversion area detectors, each of which is formed of a scintillator and an optical sensor. The optical sensor is a silicon photomultiplier (SiPM), for example. Each of the X-ray detection elements of the detector 13 outputs an electrical signal (pulse) in accordance with the incident X-ray photon. The wave-height value of the electrical signal (pulse) is correlated with the energy value of the X-ray photon. FIG. 3 is a diagram for explaining an example of the detector 13 according to the first embodiment.

FIG. 3 illustrates an enlarged view of the detector 13 illustrated in FIG. 2. FIG. 3 illustrates the detector 13 as viewed from the Y-axis side. As illustrated in FIG. 3, X-ray detection elements are arranged in a two-dimensional manner on a plane in the detector 13. For example, a plurality of lines of the X-ray detection element rows that are arranged in a channel direction (the X-axis direction in FIG. 3) are arranged along the body axis direction (the Z-axis direction in FIG. 3) of the subject P.

With reference to FIG. 2 again, the collection unit 14 collects a counting result serving as a result of counting processing using detection signals of the detector 13. The collection unit 14 counts photons (X-ray photons) derived from X-rays applied from the X-ray tube 12 and transmitted through the subject P, and collects a result of discriminating energies of the counted photons as a counting result. The collection unit 14 transmits the counting result to the console device 30.

The couch device 20 is a device on which the subject P is placed, and includes a couchtop 22 and a couch driver 21. The couchtop 22 is a plate on which the subject P is placed. The couch driver 21 moves the couchtop 22 in the Z-axis direction, so as to move the subject P into the rotary frame 15.

The frame device 10 performs, for example, helical scan to scan the subject P in a helical manner by rotating the rotary frame 15 while moving the couchtop 22. Alternatively, the frame device 10 performs conventional scan to scan the subject P with a circular track by rotating the rotary frame 15 having the position of the subject P fixed after moving the couchtop 22.

The console device 30 is a device that receives operations of the X-ray CT apparatus performed by the operator, and reconstructs X-ray CT image data using count information collected by the frame device 10. As illustrated in FIG. 1, the console device 30 includes an input device 31, a display device 32, a scan controller 33, a preprocessor 34, a projection data storage unit 35, an image reconstruction unit 36, an image storage unit 37, and a system controller 38.

The input device 31 includes a mouse or a keyboard used by the operator of the X-ray CT apparatus for inputting various instructions and various settings, and transmits information of the instructions and settings received from the operator to the system controller 38. For example, the input device 31 receives reconstruction conditions used when X-ray CT image data is reconstructed, and image processing conditions for X-ray CT image data, from the operator. In addition, for example, the input device 31 receives instructions to perform calibration of the X-ray detection elements from the operator. The input device 31 instructs the image reconstruction unit 36 to reconstruct X-ray CT image data and/or perform calibration, via the system controller 38.

The display device 32 is a monitor that is referred to by the operator. The display device 32 displays X-ray CT image data for the operator, under the control of the system controller 38, and displays graphical user interface (GUI) to receive various instructions and various settings from the operator via the input device 31.

The scan controller 33 controls operations of the high-voltage generator 11, the detector 13, the frame driver 16, the collection unit 14, and the couch driver 21, under the control of the system controller 38 described below, to control processing of collecting count information in the frame device 10. The scan controller 33 according to the first embodiment includes a calculator 33a. The details of the calculator 33a will be described in detail with reference to FIG. 7 to FIG. 9.

The preprocessor 34 performs correction processing such as logarithmic transformation, offset correction, sensitivity correction, and beam hardening correction on the counting result transmitted from the collection unit, to generate projection data for each of the energy discrimination regions.

The projection data storage unit 35 stores projection data generated by the preprocessor 34. Specifically, the projection data storage unit 35 stores projection data to reconstruct X-ray CT image data.

The image reconstruction unit 36 reconstructs a CT image based on detection signals of the detector 13. Specifically, the image reconstruction unit 36 reconstructs X-ray CT image data by performing, for example, back projection on the projection data stored in the projection data storage unit 35. An example of back projection is back projection by filtered back projection (FBP). The image reconstruction unit 36 may perform reconstruction processing by, for example, successive approximation. The image reconstruction unit 36 also performs various image processing on X-ray CT image data, to generate image data. The image reconstruction unit 36 stores the reconstructed X-ray CT image data and image data generated by various image processing in the image storage unit 37.

The projection data generated from the counting result obtained by photon counting CT includes information of energy of X-rays attenuated by being transmitted through the subject P. For this reason, the image reconstruction unit 36 can reconstruct X-ray CT image data for, for example, a specific energy component. The image reconstruction unit

36 can also reconstruct, for example, X-ray CT image data for each of a plurality of energy components.

The image reconstruction unit 36 can also allocate, for example, color tones according to energy components to pixels of X-ray CT image data of the respective energy components, to generate image data obtained by superimposing a plurality of pieces of X-ray CT image data with different colors according to energy components. The image reconstruction unit 36 can also generate image data that enables identification of a material using, for example, a K absorption edge peculiar to the material. Examples of other image data generated by the image reconstruction unit 36 are monochromatic X-ray image data, density image data, and effective atomic number image data.

The system controller 38 controls operations of the frame device 10, the couch device 20, and the console device 30, to control the whole X-ray CT apparatus. Specifically, the system controller 38 controls the scan controller 33 to control CT scan performed by the frame device 10. The system controller 38 also controls the preprocessor 34 and the image reconstruction unit 36, to control image reconstruction and image generation in the console device 30. The system controller 38 also performs control to display various image data stored in the image storage unit 37 on the display device 32.

The whole structure of the X-ray CT apparatus according to the first embodiment has been explained above. With the above structure, the X-ray CT apparatus according to the first embodiment reconstructs X-ray CT image data using the photon-counting detector.

In photon counting CT, the amount of X-rays is measured by counting the number of photons. X-rays with a larger number of photons per unit time have larger intensity. Although individual photons have different energies, photon counting CT enables acquisition of information of energy components of X-rays, by measuring energies of photons. Specifically, photon counting CT enables imaging of data collected by application of X-rays with tube voltage of a single type, for each of a plurality of energy components. For example, photon counting CT enables acquisition of image data that enables identification of a material using a difference in K absorption edge.

Figure 4:
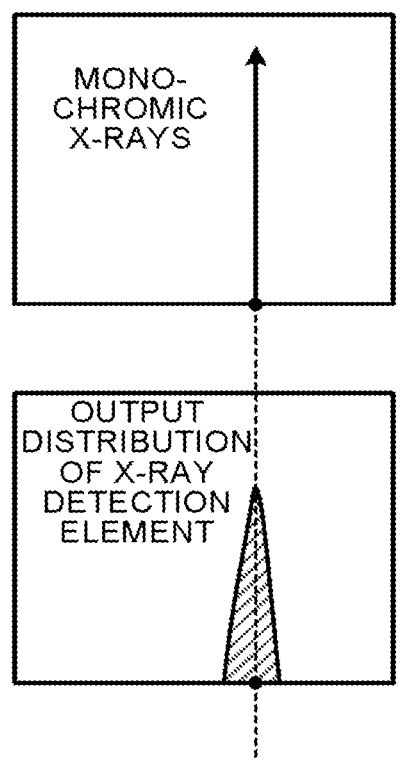
FIG. 4 is a diagram for explaining calibration processing according to related art.
Figure 5:
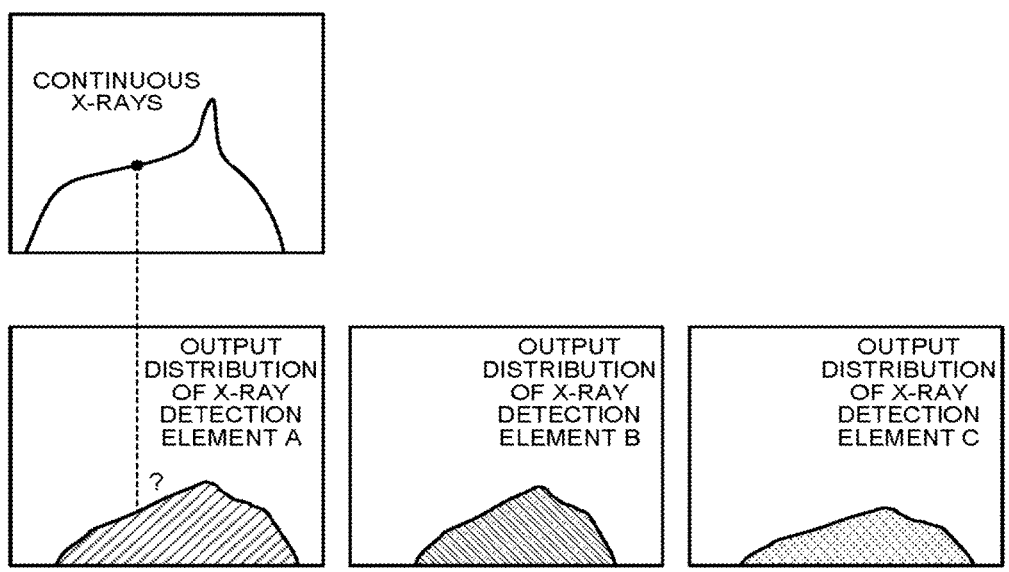
FIG. 5 is a diagram for explaining calibration processing according to related art.

Calibration processing on energy values of photons measured in the detector 13 is required, to accurately count photons by energy using the detector 13 of photon-counting type having the structure described above. FIG. 4 and FIG. 5 are diagrams for explaining calibration processing according to related art.

FIG. 4 illustrates a calibration method according to related art using an X-ray tube that can apply monochromic X-rays having known specific energy. The upper drawing of FIG. 4 illustrates an X-ray spectrum of an X-ray tube, and the lower drawing of FIG. 4 illustrates a spectrum of X-rays detected by an X-ray detection element. For example, when the X-ray tube 12 included in the X-ray CT apparatus can apply monochromic X-rays having known specific energy as illustrated in the upper drawing of FIG. 4, correlation between photon detection signals and energy values can be determined by detecting a peak of detection signals of the X-ray photons made incident on the X-ray detection element as illustrated in the lower drawing of FIG. 4.

However, the X-ray tube 12 included in the X-ray CT apparatus generates continuous X-rays having an ordinary energy distribution. For this reason, the X-ray CT apparatus cannot adopt the calibration method using an X-ray tube that can apply monochromic X-rays having known specific energy. FIG. 5 illustrates a calibration method according to related art using an X-ray tube that applies continuous X-rays having an energy distribution. The upper drawing of FIG. 5 illustrates an X-ray spectrum of the X-ray tube, and the lower drawings of FIG. 5 illustrate spectrums of X-rays detected by the X-ray detection element A to X-ray detection element C in this order from the left. As illustrated in the upper drawing of FIG. 5, the X-ray tube 12 applies continuous X-rays having an energy distribution. In addition, spectrums of detection signals of X-ray photons made incident on the respective X-ray detection elements have wide energy distributions as illustrated in the lower drawings of FIG. 5. As described above, even when continuous X-rays are applied to an X-ray detector of photon-counting type, it is difficult to detect a peak of photon detection signals with sufficient accuracy, when the energy resolution of the detector 13 is insufficient.

A calibration method used in nuclear medical imaging apparatuses is known. In the calibration method, a reference radiation source with a known energy value is disposed on each detection element. However, a long-time work is required when the method is applied to calibration of an area detector of an X-ray CT apparatus. For this reason, there is the problem that accurate and simple calibration is impossible to correct variations in X-ray energy sensitivity between X-ray detection elements.

Figure 6:
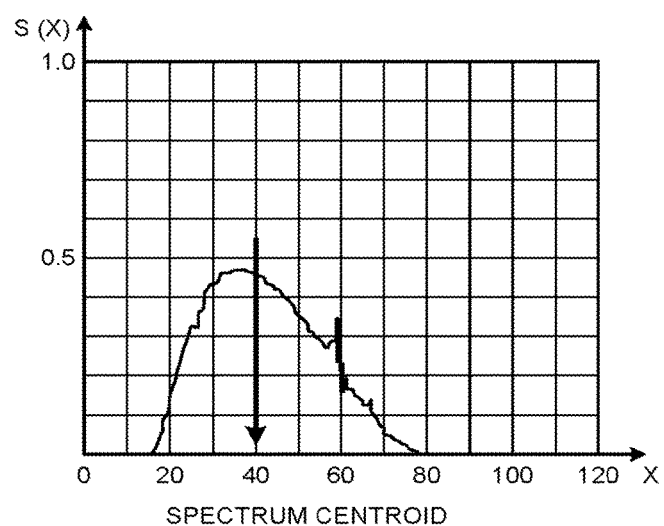
FIG. 6 is a diagram for explaining processing operations of a calculator according to the first embodiment.
Figure 7:
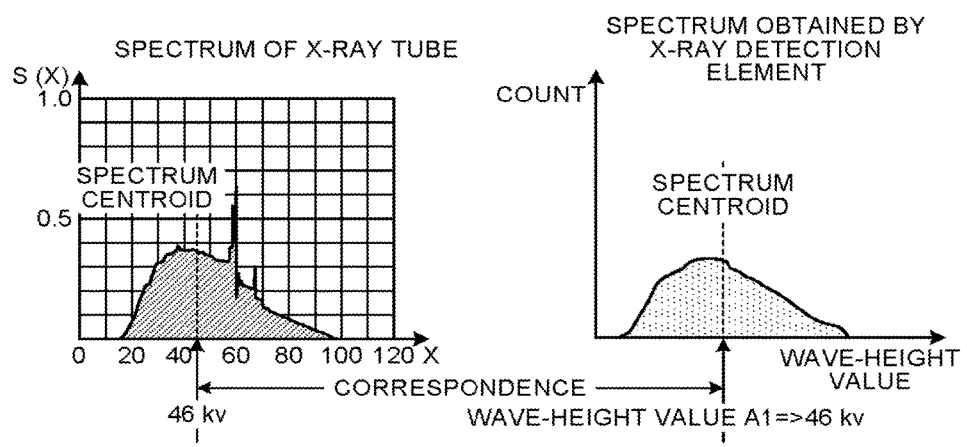
FIG. 7 is a diagram for explaining processing operations of a calculator according to the first embodiment.
Figure 8:
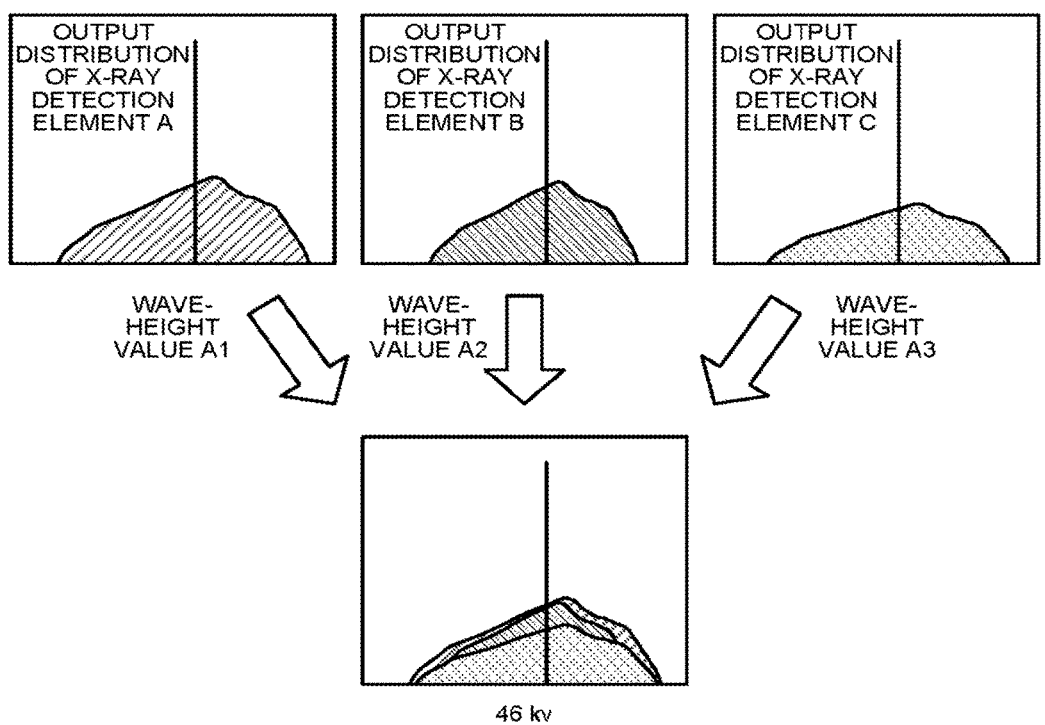
FIG. 8 is a diagram for explaining processing operations of the calculator according to the first embodiment.
Figure 9:
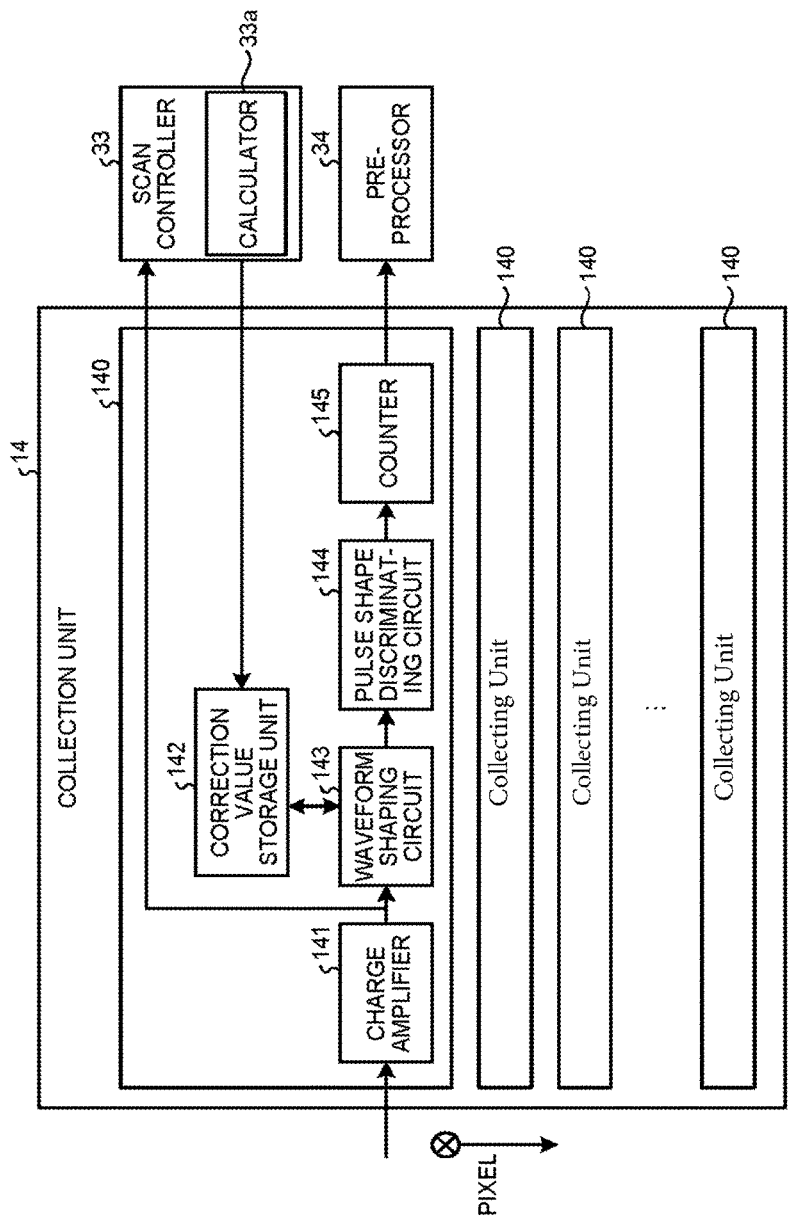
FIG. 9 is a diagram illustrating a configuration example of a collection unit according to the first embodiment.

To solve this problem, the X-ray CT apparatus according to the first embodiment corrects the detection signal detected by the detector 13 of photon-counting type for each of the X-ray detection elements, based on the centroid of the X-ray spectrum detected by the detector 13 of photon-counting type, to perform calibration accurately and simply. For example, the X-ray CT apparatus according to the first embodiment corrects the detection signal detected by the detector 13 of photon-counting type for each of the X-ray detection elements, based on a correction value calculated for each of the X-ray detection elements. Thereafter, the X-ray CT apparatus according to the first embodiment reconstructs a CT image based on the corrected detection signals. The collection unit 14 and the calculator 33a implement such function of the X-ray CT apparatus. FIG. 6 to FIG. 8 are diagrams for explaining processing operations of the calculator 33a according to the first embodiment. FIG. 9 is a diagram illustrating a configuration example of the collection unit 14 according to the first embodiment.

First, the following is explanation of processing of calculating a correction value by the calculator 33a. The calculator 33a calculates, for each of the X-ray detection elements, a correction value to cause a reference centroid serving as a centroid of a reference X-ray spectrum to match with a centroid of an X-ray spectrum detected by the detector 13 of photon-counting type. In the first embodiment, suppose that a calibrated value of a spectrometer is used as a reference X-ray spectrum.

First, the following is explanation of processing of calculating a centroid of an X-ray spectrum. In the X-ray spectrum illustrated in FIG. 6, the horizontal axis indicates an energy position (X) (unit: keV), and the vertical axis indicates a spectral intensity (S (X)) in the energy position. The term "centroid of an X-ray spectrum" here indicates the position where the area of the X-ray spectrum is equally divided. In other words, the centroid of an X-ray spectrum is the energy position where the area of X-ray spectrum in energy bands higher than the centroid is equal to the area of X-ray spectrum in energy bands lower than the centroid. For example, when the spectral intensity (S (X)) is the number of counts of X-ray photons, the centroid of an X-ray spectrum is the energy position where the number of counts of X-ray photons in energy bands higher than the centroid is equal to the number of counts of X-ray photons in energy bands lower than the centroid. The calculator 33a calculates the centroid (C) of an X-ray spectrum with the following expression "$C=\int X*S(X)dx/\int S(X)dx$", where the energy position is X, and the spectral intensity at the energy position X is S (X). For example, in the example illustrated in FIG. 6, the calculator 33a calculates the centroid of the X-ray spectrum to be the energy position of 40 keV.

FIG. 7 illustrates processing of matching a reference centroid serving as a centroid of a reference X-ray spectrum with the centroid of the X-ray spectrum detected by the detector 13. The left drawing in FIG. 7 illustrates an X-ray spectrum detected by a calibrated spectrometer, and the right drawing in FIG. 7 illustrates an X-ray spectrum detected by the X-ray detection element.

The calculator 33a determines an X-ray spectrum serving as a reference from a detection signal detected using the spectrometer, and determines a reference centroid from the reference X-ray spectrum, to calculate a correction value for each of the X-ray detection elements. For example, the calculator 33a determines an X-ray spectrum serving as a reference by measuring the spectrum of the X-ray tube 12 of the X-ray CT apparatus with a calibrated spectrometer, and determines a reference centroid by determining the centroid of the reference X-ray spectrum. In such a case, a calibrated spectrometer is disposed on the detector 13. The calibrated spectrometer measures an X-ray spectrum applied from the X-ray tube 12 under predetermined irradiation conditions. The calculator 33a obtains a measurement result via, for example, the input device 31, and calculates the reference centroid. In the example illustrated in the left drawing of FIG. 7, the calculator 33a calculates 46 keV as the reference centroid.

Next, the detector 13 detects X-rays applied from the X-ray tube 12 under the same predetermined irradiation conditions as those for the measurement of the X-ray spectrum with the calibrated spectrometer. The horizontal axis of the X-ray spectrum obtained from the detection signal that is output from each of the X-ray detection elements of the detector 13 is indicated by a wave-height value of an electrical signal (pulse) serving as the detection signal. The vertical axis of the X-ray spectrum obtained by the detection signal that is output from each of the X-ray detection signals of the detector 13 is a count value (count) of the electrical signal (pulse) serving as the detection signal. In other words, the count of the electrical signal (pulse) indicates an intensity for each wave-height value. Plotting the intensities of the respective wave-height values produces the X-ray spectrum obtained from the detection signal that is output from each of the X-ray detection elements, as illustrated in the right drawing of FIG. 7.

Thereafter, the calculator 33a determines the centroid of the X-ray spectrum illustrated in the right drawing of FIG. 7. For example, in the example illustrated in the right drawing of FIG. 7, the calculator 33a calculates the wave-height value A1 as the centroid of the X-ray spectrum. When the X-ray detection elements forming the detector 13 have low energy resolution as illustrated in the right drawing of FIG. 7, the data is blunter than the X-ray spectrum measured by the calibrated spectrometer. A count per second (CPS) of the electrical signal (pulse) serving as the detection signal may be used as a value that indicates the intensities of the respective wave-height values.

The calculator 33a determines the energy value at the wave-height value of the detector 13 at the centroid position using correspondence between the centroid of the X-ray spectrum measured by the calibrated spectrometer and the centroid of the X-ray spectrum determined from the detector 13. In the example illustrated in FIG. 7, the calculator 33a associates the wave-height value A1 with 46 keV.

The calculator 33a performs the same processing on each of the X-ray detection elements, and determines a sensitivity correction value for the same energy in each of the elements. The upper drawing in FIG. 8 illustrates respective spectrums of X-rays detected by the X-ray detection element A to the X-ray detection element C in this order from the left. The centroid of the X-ray spectrum detected by the X-ray detection element A has a wave-height value A1, the centroid of the X-ray spectrum detected by the X-ray detection element B has a wave-height value A2, and the centroid of the X-ray spectrum detected by the X-ray detection element C has a wave-height value A3.

As illustrated in the upper drawing of FIG. 8, the output waveforms of the respective X-ray detection elements have variations. The calculator 33a is capable of determining correction values for output values, by matching the centroids of the X-ray spectrums, as illustrated in the lower drawing in FIG. 8. For example, when the X-ray detection element B serves as a reference, the calculator 33a calculates that a correction value for the wave-height value of the X-ray detection element A is "A1−A2" or "A1/A2". When the X-ray detection element B serves as a reference, the calculator 33a calculates that a correction value for the wave-height value of the X-ray detection element C is "A3−A2" or "A3/A2".

Next, the collection unit 14 will be explained hereinafter. FIG. 9 is a diagram illustrating a configuration example of the collection unit 14 according to the first embodiment. As illustrated in FIG. 9, the collection unit 14 includes a plurality of collecting units 140. The collecting units 140 correspond to the respective X-ray detection elements. For this reason, the number of the collecting units 140 provided is equal to the number of the X-ray detection elements. Each of the collecting units 140 includes a charge amplifier 141, a correction value storage unit 142, a waveform shaping circuit 143, a pulse shape discriminating circuit 144, and a counter 145.

The correction value storage unit 142 stores a correction value for calibrating the detection signal of the X-ray detection element. The correction value is calculated by the calculator 33a included in the scan controller 33.

The charge amplifier 141 integrates and amplifies the electric charges that are collected in response to the photons made incident on the X-ray detection element, to output the charges as a pulse signal of the electric quantity. The pulse signal includes a peak and an area corresponding to the energy quantity of the photons.

The waveform shaping circuit 143 and the scan controller 33 are connected to the output side of the charge amplifier 141. The charge amplifier 141 switches the output of the pulse signal to one of the scan controller 33 and the waveform shaping circuit 143, in accordance with an instruction from the scan controller 33. For example, in the case of performing processing of calculating correction values for calibration, the charge amplifier 141 outputs the pulse signal to the calculator 33a of the scan controller 33. In this manner, the calculator 33a calculates correction values (see FIG. 7 and FIG. 8). By contrast, in the case of reconstructing X-ray CT image data, the charge amplifier 141 outputs the pulse signal to the waveform shaping circuit 143.

The waveform shaping circuit 143 corrects the detection signal detected by the detector 13 of photon-counting type for each X-ray detection element, based on the centroid of the X-ray spectrum detected by the detector 13 of photon-counting type. For example, the waveform shaping circuit 143 corrects the detection signal detected by the detector 13 of photon-counting type for each X-ray detection element, based on the correction value calculated for the X-ray detection element. More specifically, the waveform shaping circuit 143 shapes the waveform of the pulse signal, by regulating the frequency characteristic of the pulse signal that is output from the charge amplifier 141 and providing the signal with a gain and an offset. The pulse shape discriminating circuit 144 is connected to the output side of the waveform shaping circuit 143. The waveform shaping circuit 143 is also referred to as "correction unit".

The pulse shape discriminating circuit 144 is a circuit that compares the peak or the area of the response pulse signal to the incident photons with thresholds that are preset in correspondence with a plurality of energy bands to be discriminated, and outputs a result of comparison with the threshold to the counter 145 of the following stage.

The counter 145 counts discrimination results of waveforms of a response pulse signal for each of the corresponding energy bands, and outputs a photon counting result as digital data to the preprocessor 34 of the console device 30.

Specifically, the counter 145 collects the incident position (detection position) of the X-ray photons counted by discriminating pulses that are output from the X-ray detection element and the energy values of the X-ray photons, as a counting result, for each phase (tube phase) of the X-ray tube 12.

For example, the counting result collected by the counter 145 is information of "the count value of photons in the energy discrimination region '$E1<E\leq E2$' is 'N1', and the count value of photons in the energy discrimination region '$E2<E\leq E3$' is 'N2', in the X-ray detection element with the incident position 'P11' in the tube phase '$\alpha1$'". Alternatively, the counting result collected by the counter 145 is information of "the count value of photons per unit time in the energy discrimination region '$E1<E\leq E2$' is 'n1', and the count value of photons per unit time in the energy discrimination region '$E2<E\leq E3$' is 'n2', in the X-ray detection element with the incident position 'P11' in the tube phase '$\alpha1$'".

As described above, a counting result corresponding to a plurality of energy bands is output from the X-ray detection element corresponding to a pixel in the detector 13 as X-ray detection data to the preprocessor 34.

Figure 10:
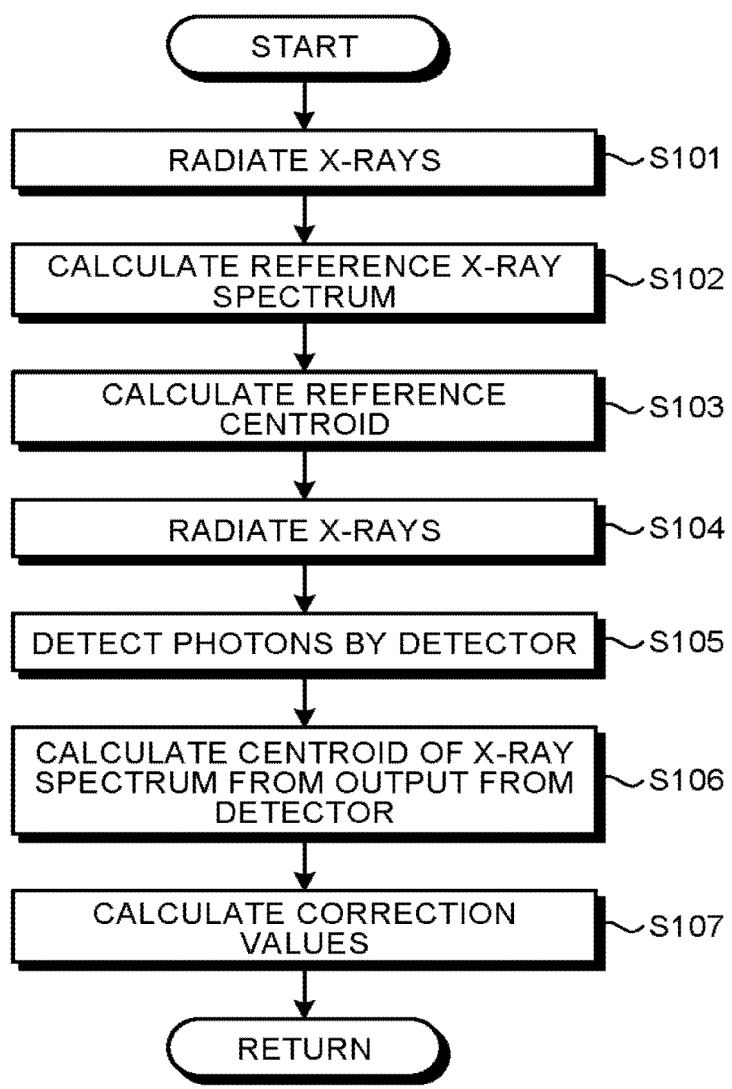
FIG. 10 is a flowchart illustrating a procedure of processing of calculating correction values by the X-ray CT apparatus according to the first embodiment.

FIG. 10 is a flowchart illustrating a procedure of processing of calculating correction values by the X-ray CT apparatus according to the first embodiment. The processing of calculating correction values is performed when, for example, the apparatus is shipped from the factory or when periodical maintenance inspection is performed. A calibrated spectrometer is disposed on the detector 13. As illustrated in FIG. 10, the scan controller 33 controls the X-ray tube 12 to cause the X-ray tube 12 to radiate X-rays (Step S101). Thereafter, the calculator 33a calculates an X-ray spectrum serving as a reference (Step S102). For example, the calculator 33a calculates an X-ray spectrum serving as a reference from a detection signal detected by using the calibrated spectrometer.

Thereafter, the calculator 33a calculates a reference centroid (Step S103). For example, the calculator 33a obtains a measurement result obtained by the calibrated spectrometer, to calculate a reference centroid serving as a centroid of the reference X-ray spectrum.

After the calibrated spectrometer is removed from the detector 13, the scan controller 33 controls the X-ray tube 12 to cause the X-ray tube 12 to radiate X-rays (Step S104). In this manner, photons are detected by the respective X-ray detection elements of the detector 13 (Step S105).

Thereafter, the calculator 33a calculates a centroid of the X-ray spectrum from the output from the detector 13 (Step S106). For example, the calculator 33a calculates the centroid of the X-ray spectrum detected by the X-ray detection element using a pulse signal that is output from the charge amplifier 141. The calculator 33a calculates correction values for the respective X-ray detection elements (Step S107). The calculator 33a stores the correction values calculated for the respective X-ray detection elements in the correction value storage units 142 of the respective collecting units 140 corresponding to the respective X-ray detection elements.

Figure 11:
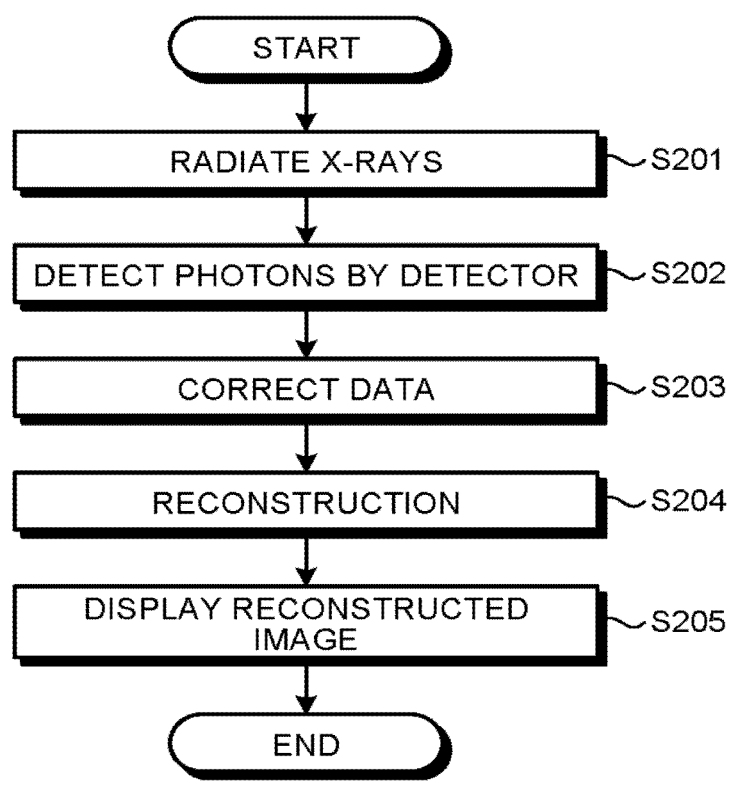
FIG. 11 is a flowchart illustrating a procedure of processing of reconstructing a CT image by the X-ray CT apparatus according to the first embodiment.

FIG. 11 is a flowchart illustrating a procedure of processing of reconstructing an X-ray CT image by the X-ray CT apparatus according to the first embodiment. As illustrated in FIG. 11, the scan controller 33 controls the X-ray tube 12 to cause the X-ray tube 12 to radiate X-rays (Step S201). In this manner, photons are detected by each of the X-ray detection elements of the detector 13 (Step S202). Thereafter, the waveform shaping circuit 143 of the collection unit 14 corrects the detection signals detected by the detector 13 of photon-counting type for the respective X-ray detection elements, based on the correction values (Step S203).

The image reconstruction unit 36 reconstructs X-ray CT image data based on the corrected detection signals (Step S204). The system controller 38 displays the reconstructed X-ray CT image on the display device 32 (Step S205).

As described above, according to the first embodiment, calibration is performed using the centroid of the X-ray spectrum. Calibration performed in this manner reduces the calculation quantity and reduces statistical errors.

Specifically, the calibration method according to the first embodiment is a simple and accurate calibration method.

For this reason, because the calibration method achieves easy calibration even if the detector 13 has a wide area and includes a large number of X-ray detection elements, the calibration method greatly reduces the number of steps of the calibration in comparison with a calibration method of related art.

In addition, the first embodiment has the structure in which a detection signal detected by the detector 13 is corrected for each of the X-ray detection elements, based on the correction value to match the reference centroid serving as the centroid of the reference X-ray spectrum with the centroid of the X-ray spectrum detected by the detector 13 of photon-counting type. This structure enables easy calibration even for X-ray detection elements, each of which is formed of an SiPM and a scintillator having resolution lower than that of direct-conversion detection elements.

The first embodiment also enables calibration by using a calibrated spectrometer in a standard configuration of an existing X-ray CT apparatus. This structure enables easy periodical calibration, and enables generation of constantly stable X-ray CT image data with accuracy.

The first embodiment illustrates that the processing of calculating correction values is performed when the apparatus is shipped from the factory or when periodical maintenance inspection is performed, but the embodiment is not limited thereto. For example, the X-ray CT apparatus may perform the processing of calculating correction values each time an X-ray CT image is reconstructed. In such a case, the X-ray CT apparatus performs the processing of reconstructing an X-ray CT image illustrated in FIG. 11, after performing the processing of calculating correction values illustrated in FIG. 10.

The calculator 33a may perform detection of X-ray signals by X-ray detection elements of the detector 13 a plurality of times, to minimize errors in measurement of the centroid of the X-ray spectrum. This structure enables the calculator 33a to further enhance the accuracy of correction values calculated for the respective X-ray detection elements.

Modification of First Embodiment

The first embodiment described above illustrates the case of calibrating the centroid of the X-ray spectrum detected by the detector 13, by measuring the X-ray spectrum radiated from the X-ray tube 12 under predetermined irradiation conditions, but the embodiment is not limited thereto. For example, each of the X-ray detection elements has variations in sensitivity according to the maximum energy generated in accordance with the tube voltage supplied to the X-ray tube 12. For this reason, it is preferable to perform calibration for each tube voltage used in imaging, to perform more accurate measurement.

Figure 12:
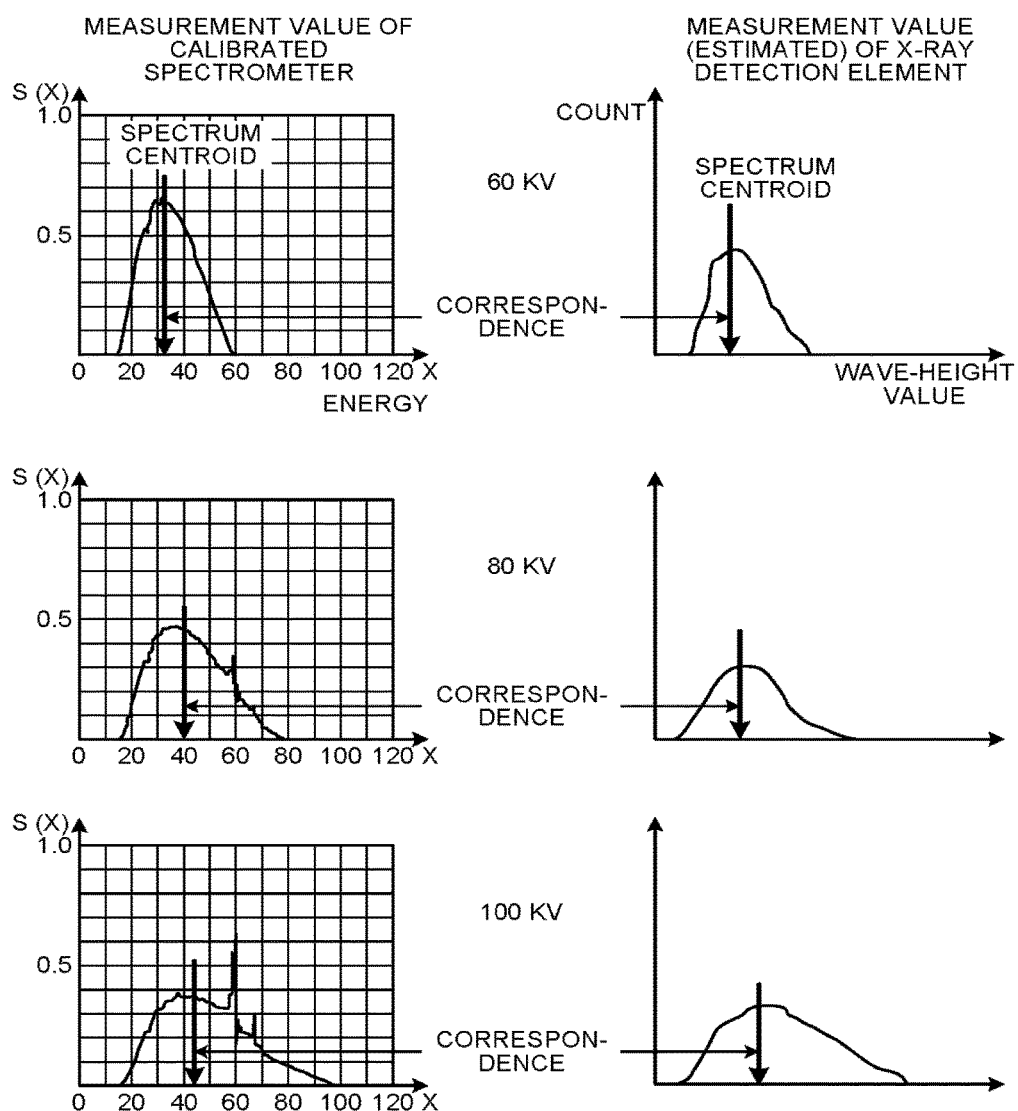
FIG. 12 is a diagram for explaining processing operations of the X-ray CT apparatus according to a modification of the first embodiment.

In view of the above, the modification of the first embodiment illustrates the case of performing calibration according to the tube voltage of the X-ray tube 12, and calculating calibration data in accordance with each tube voltage of the X-ray tube 12 for each of the X-ray detection elements. FIG. 12 is a diagram for explaining processing operations of the X-ray CT apparatus according to the modification of the first embodiment.

FIG. 12 illustrates the cases where the tube voltage of the X-ray tube 12 is 60 kV, 80 kV, and 100 kV. The upper left drawing in FIG. 12 illustrates a spectrum of X-rays measured by a calibrated spectrometer in the case where the tube voltage is 60 kV, and the upper right drawing in FIG. 12 illustrates a spectrum of X-rays detected by the X-ray detection element of the detector 13 in the case where the tube voltage is 60 kV. As illustrated in the upper left drawing in FIG. 12, when the tube voltage is 60 kV, the maximum energy of the spectrum of the X-rays measured by the calibrated spectrometer is 60 keV. In such a case, the calculator 33a calculates that the reference centroid is the energy position of 32 keV. The calculator 33a associates the wave-height value of the centroid of the X-ray spectrum detected by the X-ray detection element of the detector 13 with the reference centroid.

The middle left drawing in FIG. 12 illustrates a spectrum of X-rays measured by a calibrated spectrometer in the case where the tube voltage is 80 kV, and the middle right drawing in FIG. 12 illustrates a spectrum of X-rays detected by the X-ray detection element of the detector 13 in the case where the tube voltage is 80 kV. As illustrated in the middle left drawing in FIG. 12, when the tube voltage is 80 kV, the maximum energy of the spectrum of the X-rays measured by the calibrated spectrometer is 80 keV. In such a case, the calculator 33a calculates that the reference centroid is the energy position of 40 keV. The calculator 33a associates the wave-height value of the centroid of the X-ray spectrum detected by the X-ray detection element of the detector 13 with the reference centroid.

The lower left drawing in FIG. 12 illustrates a spectrum of X-rays measured by a calibrated spectrometer in the case where the tube voltage is 100 kV, and the lower right drawing in FIG. 12 illustrates a spectrum of X-rays detected by the X-ray detection element of the detector 13 in the case where the tube voltage is 100 kV. As illustrated in the lower left drawing in FIG. 12, when the tube voltage is 100 kV, the maximum energy of the spectrum of the X-rays measured by the calibrated spectrometer is 100 keV. In such a case, the calculator 33a calculates that the reference centroid is the energy position of 43 keV. The calculator 33a associates the wave-height value of the centroid of the X-ray spectrum detected by the X-ray detection element of the detector 13 with the reference centroid.

The calculator 33a may perform detection of X-ray signals by X-ray detection elements of the detector 13 a plurality of times in each tube voltage, to minimize errors in measurement of the centroid of the X-ray spectrum. This structure enables the calculator 33a to further enhance the accuracy of correction values calculated for the respective X-ray detection elements.

Second Embodiment

The first embodiment illustrates the structure of measuring a reference X-ray spectrum using a calibrated spectrometer. Each of the X-ray detection elements can be calibrated by using a reference detection element configured to have higher energy resolution than that of the X-ray detection elements included in the detector 13, to detect a reference X-ray spectrum, instead of using a separate measurement device such as a calibrated spectrometer. For this reason, the second embodiment illustrates the case of using and incorporating a reference detection element having high energy resolution in the detector 13.

The configuration of an X-ray CT apparatus according to the second embodiment is the same as the configuration of the X-ray CT apparatus illustrated in FIG. 1, except for the configuration of the X-ray detection elements included in the detector 13, the configuration of the collection unit 14, and the configuration of the scan controller 33. For this reason, the following explanation illustrates only the configuration of the detector 13 according to the second embodiment, the configuration of the collection unit 14 according to the second embodiment, and the configuration of the scan controller 33 according to the second embodiment. In the X-ray CT apparatus according to the second embodiment, only the detector 13 is movable on the rotary frame 15.

FIG. 13 is a diagram for explaining an example of the detector 13 according to the second embodiment. FIG. 13 illustrates the detector 13 as viewed from the Y-axis side. X-ray detection elements are arranged in a two-dimensional manner on a surface of the detector 13. For example, a plurality of lines of the X-ray detection element rows that are arranged in a channel direction (the X-axis direction in FIG. 13) are arranged along the body axis direction (the Z-axis direction in FIG. 13) of the subject P. The example of FIG. 13 illustrates a plurality of X-ray detection elements that are arranged along the body axis direction as an X-ray detection element group.

As illustrated in FIG. 13, the detector 13 according to the second embodiment includes an X-ray detection element group 13a and a plurality of X-ray detection element groups 13b. In the example illustrated in FIG. 13, the X-ray detection element group 13a is disposed in one end portion in the channel direction in the detector 13. Each of the X-ray detection elements of the X-ray detection element groups 13b is an indirect-conversion detector formed of a scintillator and an optical sensor. The optical sensor is, for example, an SiPM. Each of the X-ray detection elements of the X-ray detection element group 13a is a reference detection element having higher energy resolution than that of each of the X-ray detection elements of the X-ray detection element groups 13b. Each of the X-ray detection elements of the X-ray detection element group 13a is, for example, a direct-conversion detector that can be formed of a cadmium telluride (CdTe) semiconductor or a cadimium zinc telluride (CdZnTe) semiconductor.

Figure 14:
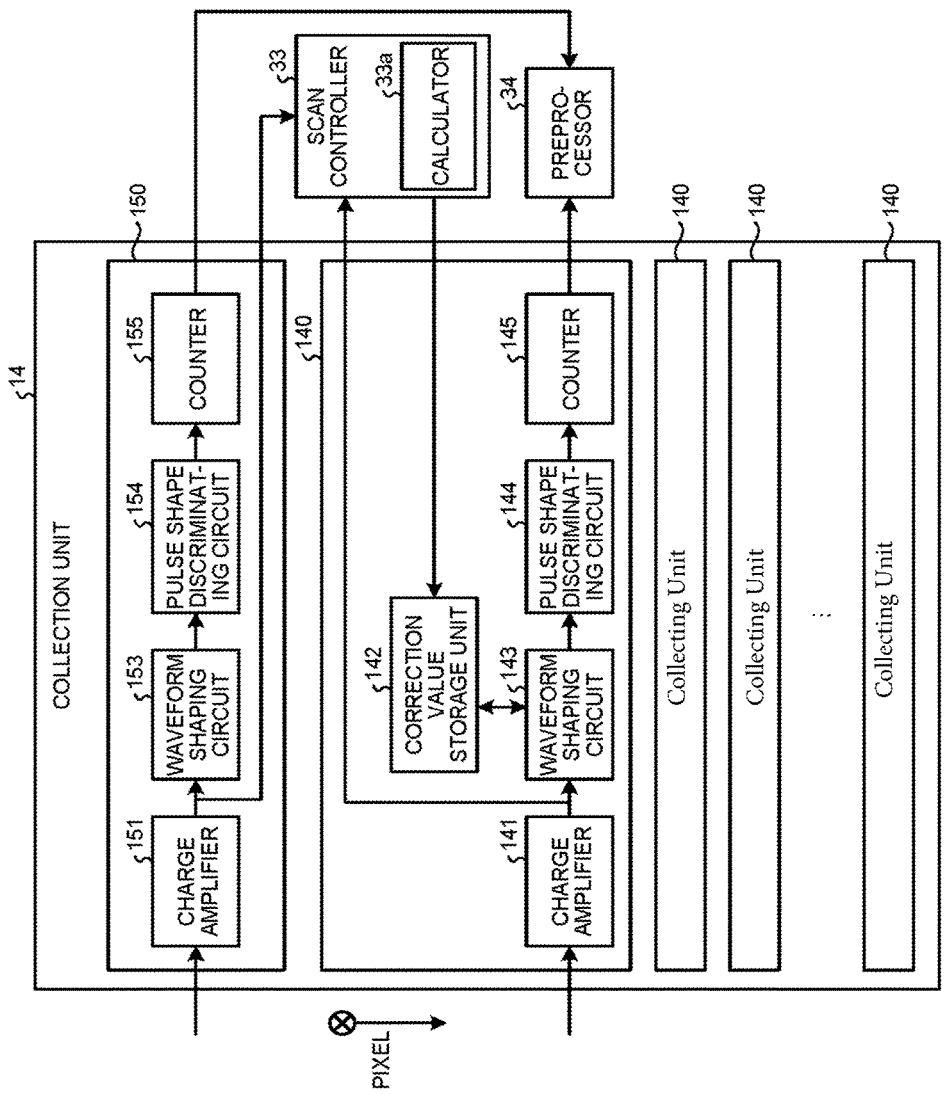
FIG. 14 is a diagram illustrating a configuration example of a collection unit according to the second embodiment.

FIG. 14 is a diagram illustrating a configuration example of the collection unit 14 according to the second embodiment. As illustrated in FIG. 14, the collection unit 14 includes collecting units 140, and collecting units 150.

The collecting units 140 correspond to the respective X-ray detection elements of the X-ray detection element groups 13b. For this reason, the number of the collecting units 140 provided is equal to the number of the X-ray detection elements of the X-ray detection element groups 13b. Each of the collecting units 140 includes a charge amplifier 141, a correction value storage unit 142, a waveform shaping circuit 143, a pulse shape discriminating circuit 144, and a counter 145. The functions of the units included in each of the collecting units 140 according to the second embodiment are the same as the functions of the units included in each of the collecting units 140 according to the first embodiment.

The collecting units 150 correspond to the respective X-ray detection elements of the X-ray detection element group 13a. For this reason, the number of the collecting units 150 provided is equal to the number of the X-ray detection elements of the X-ray detection element group 13a. Each of the collecting units 150 includes a charge amplifier 151, a waveform shaping circuit 153, a pulse shape discriminating circuit 154, and a counter 155.

The charge amplifier 151 integrates and amplifies the electric charges that are collected in response to the photons made incident on each X-ray detection element of the X-ray detection element group 13a, to output the charges as a pulse signal of the electric quantity. The waveform shaping circuit 153 and the scan controller 33 are connected to the output side of the charge amplifier 151. In the case of performing processing of calculating correction values, the charge amplifier 151 outputs the pulse signal to the calculator 33a of the scan controller 33. In this manner, the calculator 33a calculates correction values. By contrast, in the case of using pixels corresponding to the reference detection elements disposed in one end portion in the channel direction for reconstructing an X-ray CT image, the charge amplifier 151 outputs the pulse signal to the waveform shaping circuit 153.

The waveform shaping circuit 153 shapes the waveform of the pulse signal, by regulating the frequency characteristic of the pulse signal that is output from the charge amplifier 151 and providing the signal with a gain and an offset.

The pulse shape discriminating circuit 154 is a circuit that compares the peak or the area of the response pulse signal to the incident photons with thresholds that are preset in correspondence with a plurality of energy bands to be discriminated, and outputs a result of the comparison with the threshold to the counter 155 of the following stage.

The counter 155 counts discrimination results of waveforms of a response pulse signal for each of the corresponding energy bands, and outputs a photon counting result as digital data to the preprocessor 34 of the console device 30.

Figure 15:
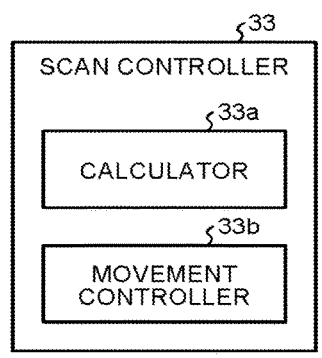
FIG. 15 is a diagram illustrating a configuration example of a scan controller according to the second embodiment.

FIG. 15 is a diagram illustrating a configuration example of the scan controller 33 according to the second embodiment. As illustrated in FIG. 15, the scan controller 33 according to the second embodiment includes the calculator 33a and a movement controller 33b.

Figure 16:
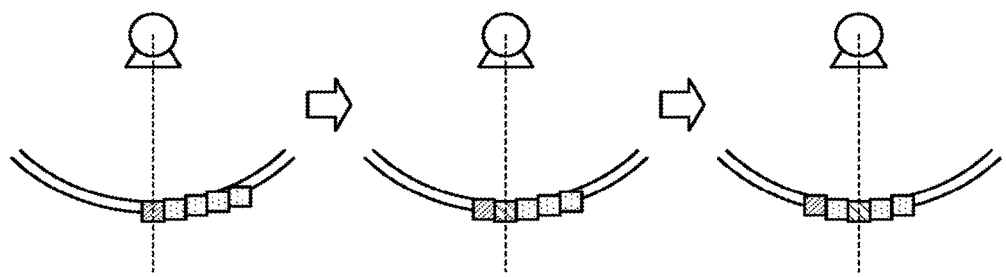
FIG. 16 is a diagram for explaining processing operations of a movement controller according to the second embodiment.

The movement controller 33b controls movement of the detector 13 in the channel direction independently of the X-ray tube 12. In other words, the movement controller 33b moves only the detector 13 in the channel direction on the rotary frame 15. FIG. 16 is a diagram for explaining processing operations of the movement controller 33b according to the second embodiment. The left drawing in FIG. 16 illustrates the case where the reference detection elements are placed in a position opposed to the X-ray tube 12. In this state, the X-ray tube 12 radiates X-rays, and the reference detection elements detect an X-ray spectrum. Specifically, the movement controller 33b places the reference detection elements in a position opposed to the X-ray tube 12 when determining the reference centroid.

Thereafter, the movement controller 33b moves the detector 13 in the channel direction. In this manner, the X-ray detection elements of the X-ray detection element group 13b disposed next to the reference detection elements are placed in the position opposed to the X-ray tube 12, as illustrated in the middle drawing in FIG. 16. In this state, the X-ray tube 12 radiates X-rays, and the X-ray detection elements of the X-ray detection element group 13b detect an X-ray spectrum. Specifically, the movement controller 33b places the X-ray detection elements to be corrected in the position opposed to the X-ray tube 12, when the centroid of the X-ray spectrum is determined from the detection signals detected by the X-ray detection elements to be corrected.

In the same manner, the movement controller 33b moves the detector 13 in the channel direction. In this manner, the X-ray detection elements of the X-ray detection element group 13b disposed in the second position from the reference detection elements are placed in the position opposed to the X-ray tube 12, as illustrated in the right drawing in FIG. 16. In this state, the X-ray tube 12 radiates X-rays, and the X-ray detection elements of the X-ray detection element group 13b detect an X-ray spectrum. Specifically, the movement controller 33b places the X-ray detection elements to be corrected in the position opposed to the X-ray tube 12, when the centroid of the X-ray spectrum is determined from the detection signals detected by the X-ray detection elements to be corrected. As described above, the movement controller 33b moves the position of the detector 13 in the channel direction, without moving the position of the X-ray tube 12. In addition, the movement controller 33b performs control such that the position of the reference detection elements in the channel direction when the reference centroid is determined agrees with the position of the X-ray detection elements to be corrected in the channel direction when the centroid of the X-ray spectrum is determined from the detection signals detected by the X-ray detection elements to be corrected.

Figure 17:
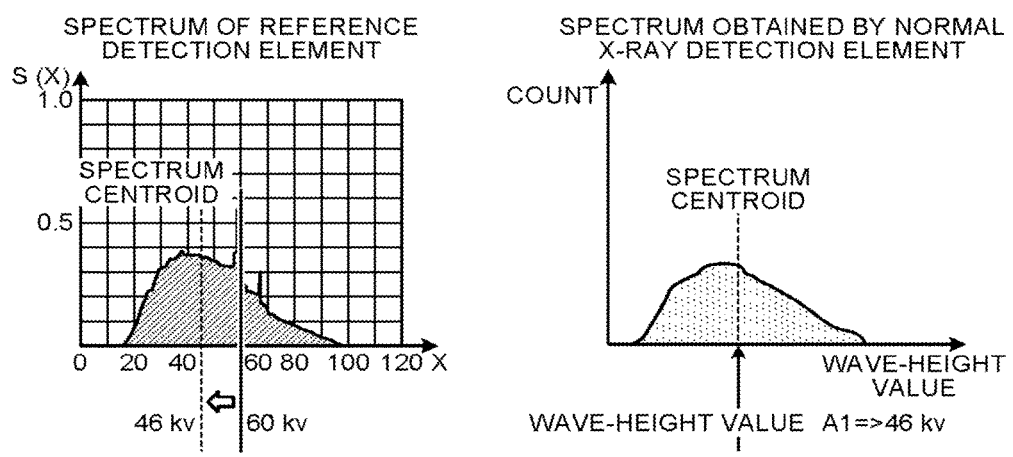
FIG. 17 is a diagram for explaining processing operations of a calculator according to the second embodiment.

The calculator 33a according to the second embodiment determines an X-ray spectrum serving as a reference from detection signals detected using the reference detection elements, and determines a reference centroid based on the characteristic X-rays of the reference X-ray spectrum, to calculate correction values for the respective X-ray detection elements. FIG. 17 is a diagram for explaining processing operations of the calculator 33a according to the second embodiment.

The left drawing in FIG. 17 illustrates an X-ray spectrum measured by the reference detection elements, and the right drawing in FIG. 17 illustrates an X-ray spectrum detected by the X-ray detection elements of the X-ray detection element group 13b. The X-ray spectrum measured by the reference detection elements are indicated by the wave-height value and the count. In other words, the X-ray spectrum measured by the reference detection elements is not measured as an energy value. For this reason, the calculator 33a according to the second embodiment associates the wave-height value of the X-ray spectrum measured by the reference detection elements with the energy value.

In this example, suppose that the characteristic X-rays of the X-ray tube 12 have a known energy value. For example, the calculator 33a specifies the characteristic X-rays of the reference X-ray spectrum measured by the reference detection elements, and associates the wave-height value of the specified characteristic X-rays with the energy value. This example illustrates the case where the characteristic X-rays of the X-ray spectrum have 60 keV. The calculator 33a also determines a reference centroid serving as the centroid of the reference X-ray spectrum. The calculator 33a calculates an energy value corresponding to the wave-height value of the reference centroid, based on the energy value of the specified characteristic X-rays. In the example illustrated in the left drawing in FIG. 17, the calculator 33a calculates 46 keV as the reference centroid.

Thereafter, the calculator 33a calculates the centroid of the X-ray spectrum detected by the X-ray detection elements of the X-ray detection element group 13b. In the example illustrated in the right drawing in FIG. 17, the calculator 33a calculates the wave-height value A1 as the centroid of the X-ray spectrum. The calculator 33a associates the wave-height value A1 with 46 keV.

The procedure of processing of reconstructing an X-ray CT image by the X-ray CT apparatus according to the second embodiment is the same as the procedure of processing illustrated in FIG. 10, except for the details of the processing of calculating correction values in Step S102. For this reason, the following explanation illustrates only a procedure of the processing of calculating correction values by the X-ray CT apparatus according to the second embodiment, with reference to FIG. 18.

Figure 18:
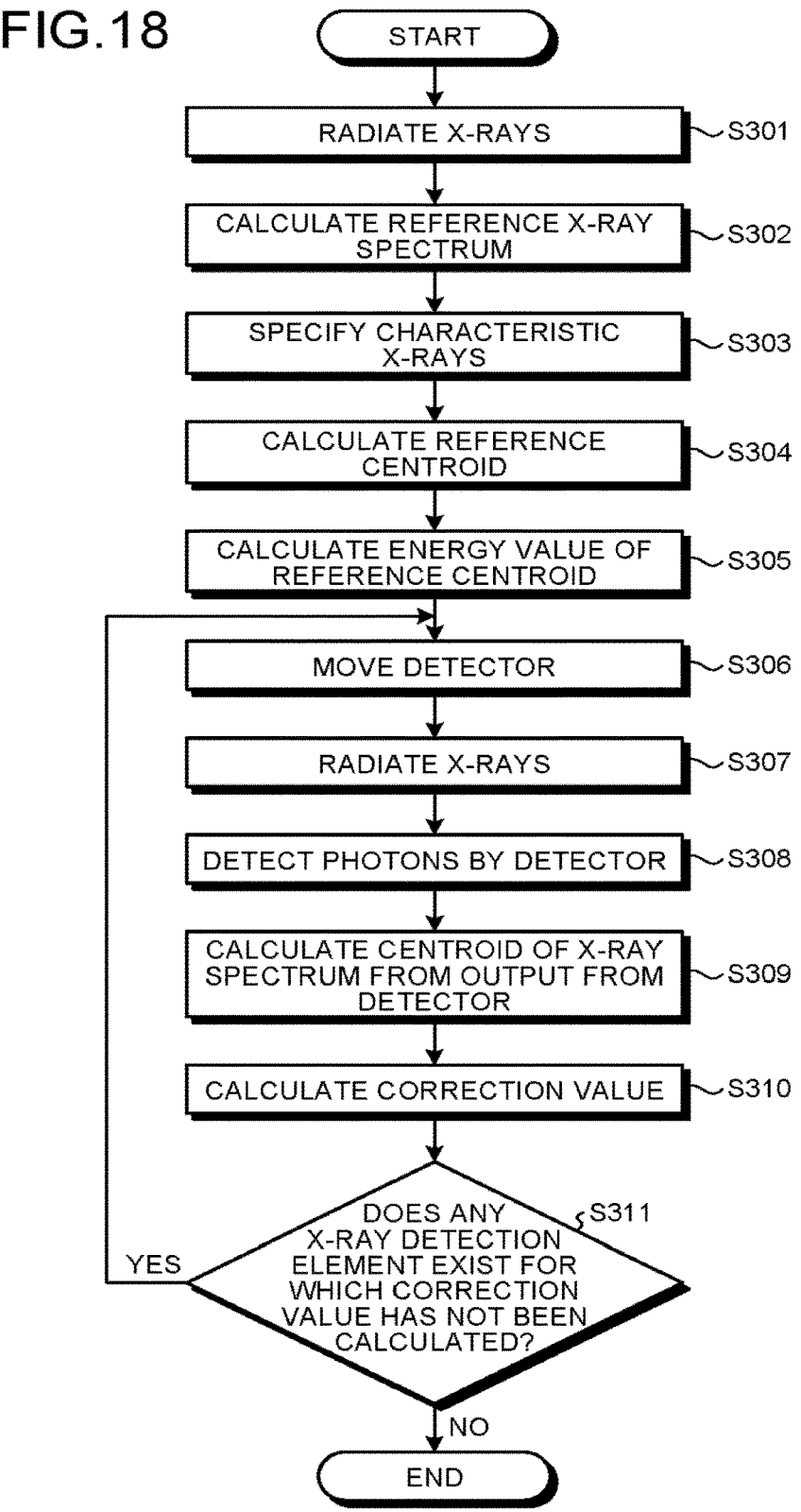
FIG. 18 is a flowchart illustrating a procedure of processing of calculating correction values by the X-ray CT apparatus according to the second embodiment.

FIG. 18 is a flowchart illustrating a procedure of processing of calculating correction values by the X-ray CT apparatus according to the second embodiment. The processing corresponds to the processing in Step S102 illustrated in FIG. 10. The example in FIG. 18 illustrates the case where X-ray detection elements having high energy resolution are placed in a position opposed to the X-ray tube 12, at the time of starting the processing of calculating correction values.

As illustrated in FIG. 18, the scan controller 33 controls the X-ray tube 12 to cause the X-ray tube 12 to radiate X-rays (Step S301). The calculator 33a calculates an X-ray spectrum serving as a reference (Step S302). For example, the calculator 33a calculates an X-ray spectrum serving as a reference from a detection signal detected by using the X-ray detection element having high energy resolution.

Thereafter, the calculator 33a specifies characteristic X-rays of the reference X-ray spectrum (Step S303). For example, the calculator 33a obtains a measurement result obtained by the X-ray detection element having high energy resolution, and associates the wave-height value of the characteristic X-rays with an energy value of known characteristic X-rays. The calculator 33a also calculates a reference centroid (Step S304). For example, the calculator 33a obtains a measurement result obtained by the X-ray detection element having high energy resolution, and calculates the reference centroid. The calculator 33a calculates an energy value of the reference centroid based on the specified energy value of the characteristic X-rays (Step S305).

Thereafter, the movement controller 33b moves the detector 13 by one detection element group (Step S306). The scan controller 33 controls the X-ray tube 12 to cause the X-ray tube 12 to radiate X-rays (Step S307). In this manner, photons are detected by the X-ray detection element that is placed in the position opposed to the X-ray tube 12 among the X-ray detection elements of the detector 13 (Step S308).

Thereafter, the calculator 33a calculates a centroid of the X-ray spectrum from an output from the X-ray detection element placed in the irradiation position among the X-ray detection elements of the detector 13 (Step S309). For example, the calculator 33a calculates the centroid of the X-ray spectrum detected by the X-ray detection element using a pulse signal that is output from the charge amplifier 141 corresponding to the X-ray detection element placed in the irradiation position. The calculator 33a calculates a correction value of the X-ray detection element placed in the irradiation position (Step S310). The calculator 33a stores the correction value calculated for the X-ray detection element placed in the irradiation position in the correction value storage unit 142 of the collecting unit 140 corresponding to the X-ray detection element.

Thereafter, the scan controller 33 determines whether any X-ray detection element exists for which a correction value has not been calculated (Step S311). When the scan controller 33 determines that an X-ray detection element exists for which a correction value has not been calculated (Yes at Step S311), the scan controller 33 goes to Step S306. The movement controller 33b moves the detector 13 by one detection element group, and calculates a correction value of the X-ray detection element placed in the irradiation position. By contrast, when the scan controller 33 determines that no X-ray detection element exists for which a correction value has not been calculated (No at Step S311), the scan controller 33 ends the processing of calculating correction values.

As described above, according to the second embodiment, detection signals detected by the detector 13 are corrected for the respective X-ray detection elements, based on a correction value to match the reference centroid serving as the centroid of the reference X-ray spectrum with the centroid of the X-ray spectrum detected by the detector 13 of photon-counting type. Calibration using the centroid of the X-ray spectrum reduces the calculation quantity and reduces statistical errors. Specifically, the calibration method according to the second embodiment is a simple and accurate calibration method.

X-ray detection elements having high energy resolution, such as CdTe, are expensive and difficult to mass produce. For this reason, CdTe has not become widespread enough to be used for large-sized area detectors. In practice, reconstruction of actual X-ray CT images does not necessarily require energy resolution as much as that of CdTe. However, proper calibration is required even for X-ray detection elements having energy resolution inferior to that of CdTe. The second embodiment has the structure in which reference detection elements having high energy resolution is incorporated in the detector 13, and detection signals detected by the detector 13 are corrected for the respective X-ray detection elements, based on the centroid of the X-ray spectrum measured by the reference detection elements having high energy resolution. In addition, the second embodiment has the structure in which detection signals detected by X-ray detection elements, each of which is formed of an inexpensive SiPM and a scintillator, are corrected for the respective X-ray detection elements, to reconstruct an X-ray CT image. With these structures, the second embodiment enables both reduction in cost and collection of image data with high accuracy.

The second embodiment illustrates the case of including the reference detection elements in the detector 13, but the embodiment is not limited thereto. For example, the reference detection elements may be arranged in a place other than the detector 13, as long as the reference detection elements in the place can measure an X-ray spectrum applied from the X-ray tube 12. In such a case, the calculator 33a calculates the centroid of the X-ray spectrum, by calibrating the detection signals of the reference detection elements to detection signals in the case where the reference detection elements are placed in the position opposed to the X-ray tube 12.

The second embodiment illustrates that the reference detection elements are arranged in one end portion in the channel direction in the detector 13, but the embodiment is not limited thereto. For example, the reference detection elements may be arranged in any desired position in the detector 13, such as a central portion in the channel direction thereof. When the reference detection elements are arranged in one end portion in the channel direction in the detector 13, detection signals from the reference detection elements are not necessarily used for reconstruction of an X-ray CT image.

FIG. 22 is a diagram (1) for explaining another example of the detector according to the second embodiment, and FIG. 23 is a diagram (2) for explaining another example of the detector according to the second embodiment. In the example illustrated in FIG. 22, X-ray detection element groups 13a are arranged in both end portions in the channel direction in the detector 13. In the example illustrated in FIG. 23, X-ray detection element groups 13a are arranged in both end portions in the channel direction in the detector 13, and in a central portion in the channel direction in the detector 13.

Modification of Second Embodiment

The above embodiment illustrates the case of performing calibration with the reference detection elements placed in the position opposed to the X-ray tube 12, but the embodiment is not limited thereto. For example, in the detector 13, when the position opposed to the X-ray tube 12 is defined as a central portion and positions around the central portion are defined as peripheral portions, the radiation quality of X-rays detected in the central portion is different from the radiation quality of X-rays detected in the peripheral portions. In addition, the radiation qualities of detected X-rays are different between positions in the peripheral portions. In other words, the radiation quality of detected X-rays varies according to the relative positional relation between the X-ray tube 12 and each of the X-ray detection elements.

Figure 24:
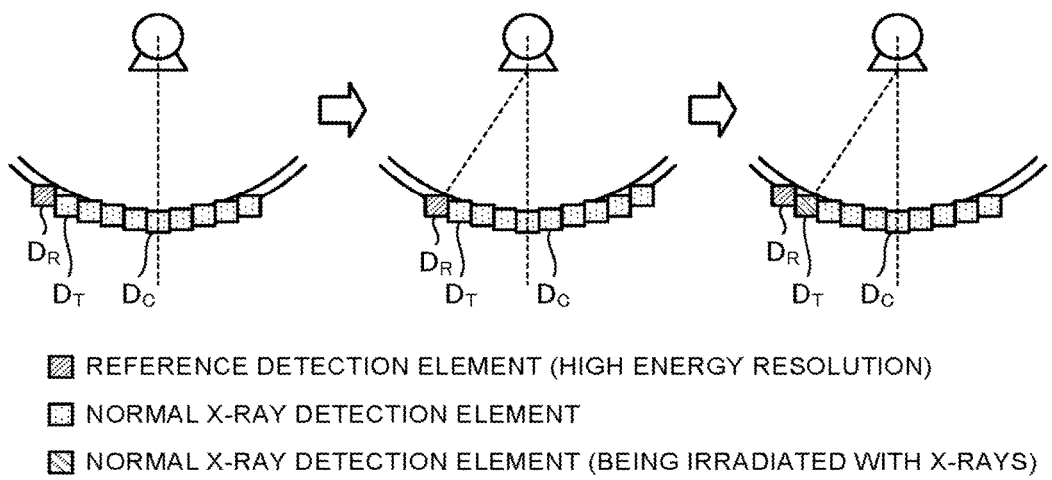
FIG. 24 is a diagram for explaining processing operations of a movement controller according to a modification of the second embodiment.

In view of the above, calibration should be performed while the relative position between the X-ray tube 12 and each of the X-ray detection elements of the X-ray detection element group 13b is maintained. For this reason, a modification of the second embodiment will be explained hereinafter. The modification illustrates the case of performing calibration while the relative position between the X-ray tube 12 and each of the X-ray detection elements is maintained. The configuration of the X-ray CT apparatus according to the modification of the second embodiment is the same as the configuration of the X-ray CT apparatus according to the second embodiment, except for part of the function of the movement controller 33b. FIG. 24 is a diagram for explaining processing operations of the movement controller 33b according to the modification of the second embodiment.

FIG. 24 illustrates the case where the reference detection elements are arranged at the left end serving as one end portion in the channel direction, in the same manner as the detector 13 illustrated in FIG. 13. FIG. 24 also illustrates the case of calibrating the X-ray detection element $D_T$ arranged on the right side of the reference detection element $D_R$ in the channel direction. In the left drawing in FIG. 24, the X-ray detection element $D_c$ disposed in the center of the detector 13 is placed in the position opposed to the X-ray tube 12. The state in the left drawing in FIG. 24 is an initial state.

The movement controller 33b controls movement of the detector 13 in the channel direction independently of the X-ray tube 12. The movement controller 33b performs control such that the position of the reference detection element in the channel direction when the reference centroid is determined matches with the position in the channel direction of the X-ray detection element to be corrected when the centroid of the X-ray spectrum is determined.

For example, the movement controller 33b moves the detector 13 toward the right in the channel direction by a distance corresponding to one X-ray detection element. In the movement, the movement controller 33b moves the position of the detector 13 in the channel direction, without moving the position of the X-ray tube 12, in the same manner as in the second embodiment. In this manner, the reference detection element $D_R$ is moved to a position where the X-ray detection element $D_T$ was placed before the movement. In this state, the X-ray tube 12 radiates X-rays, and the reference detection element $D_R$ detects the X-ray spectrum. Specifically, when the reference centroid is determined, the movement controller 33b places the reference detection element $D_R$ in a position agreeing with the relative position between the X-ray detection element $D_T$ to be corrected and the X-ray tube 12, in a state where the center of the detector 13 of photon-counting type is opposed to the X-ray tube 12.

Thereafter, the movement controller 33b moves the detector 13 toward the left in the channel direction by a distance corresponding to one X-ray detection element. Also in such a case, the movement controller 33b moves the position of the detector 13 in the channel direction, without moving the position of the X-ray tube 12, in the same manner as in the second embodiment. In this manner, the X-ray detection element $D_T$ is placed in the same position as that in the initial state. In this state, the X-ray tube 12 radiates X-rays, and the X-ray detection element $D_T$ detects the X-ray spectrum. Specifically, when the centroid of the X-ray spectrum is determined from the detection signal detected by the X-ray detection element $D_T$ to be corrected, the movement controller 33b places the center of the detector 13 of photon-counting type in the position opposed to the X-ray tube 12.

The calculator 33a according to the second embodiment determines an X-ray spectrum serving as a reference from the detection signal detected using the reference detection element $D_R$, and determines the reference centroid based on characteristic X-rays of the reference X-ray spectrum, to calculate a correction value of the X-ray detection element $D_T$. With the structure, the modification of the second embodiment enables calibration, while maintaining the relative positions between the X-ray tube 12 and each of the X-ray detection elements of the X-ray detection element group 13b.

The modification of the second embodiment described above illustrates that the reference detection element $D_R$ is moved to the position where the X-ray detection element $D_T$ to be calibrated is disposed in the initial state, X-rays are applied, and thereafter the position is returned to the initial state to apply X-rays to the X-ray detection element $D_T$ to be calibrated, but the embodiment is not limited thereto. Specifically, the detector 13 may be moved in any desired order, as long as the reference detection element $D_R$ is moved while the relative position is maintained between the X-ray tube 12 and the X-ray detection element to be calibrated. For example, the X-ray tube 12 applies X-rays in the initial state, and each of the X-ray detection elements to be calibrated detects an X-ray spectrum. Thereafter, after the reference detection element $D_R$ is moved to the position where the X-ray detection element to be calibrated was placed in the initial state, the X-ray tube 12 applies X-rays, and the reference detection element $D_R$ detects an X-ray spectrum. The movement controller 33b repeats the processing in the predetermined order, until the reference detection element $D_R$ detects an X-ray spectrum in all the positions where the X-ray detection elements to be calibrated are arranged in the initial state.

In addition, the modification of the second embodiment illustrates the case of using the detector 13 similar to that illustrated in FIG. 13, but the embodiment is not limited thereto. For example, the detector 13 as illustrated in FIG. 22 and FIG. 23 may be used. In such a case, because calibration can be performed using a plurality of reference detection elements, the structure reduces the number of movements of the detector 13 and the number of radiations of X-rays.

Third Embodiment

Figure 19:
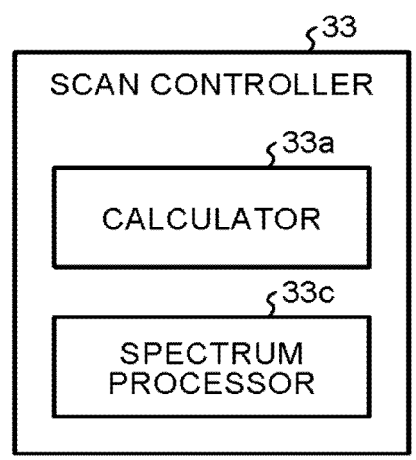
FIG. 19 is a diagram illustrating a configuration example of a scan controller according to a third embodiment.

The above embodiments illustrate that the calculator 33a calculates a centroid using an X-ray spectrum detected by the calibrated spectrometer or the reference detection elements without any processing, but the embodiments are not limited thereto. For example, the calculator 33a may calculate a centroid for an X-ray spectrum that has been subjected to preprocessing such as noise removal. FIG. 19 is a diagram illustrating a configuration example of the scan controller according to the third embodiment.

Figure 20:
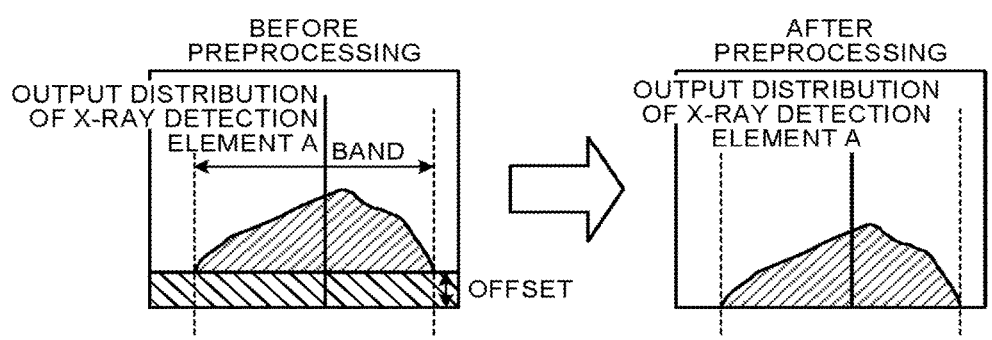
FIG. 20 is a diagram for explaining processing operations of a spectrum processor according to the third embodiment.
Figure 21:
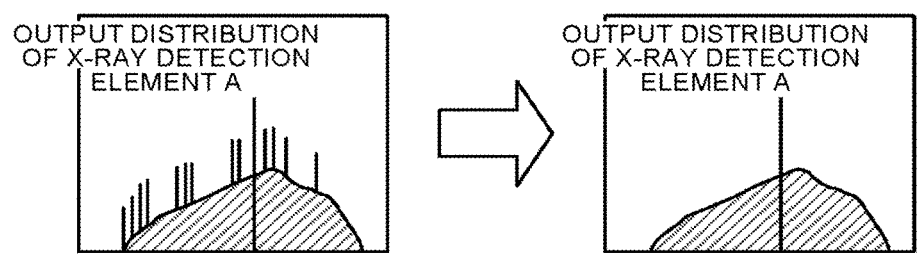
FIG. 21 is a diagram for explaining processing operations of the spectrum processor according to the third embodiment.

As illustrated in FIG. 19, the scan controller 33 according to the third embodiment includes the calculator 33a, and a spectrum processor 33c. The spectrum processor 33c preprocesses the X-ray spectrum serving as a reference. FIG. 20 and FIG. 21 are diagrams for explaining processing operations of the spectrum processor 33c according to the third embodiment. Although FIG. 20 and FIG. 21 illustrate the case of preprocessing an X-ray spectrum detected by the reference detection elements, the same processing is applicable to an X-ray spectrum detected by a calibrated spectrometer.

FIG. 20 illustrates a processing of removing an offset. The left drawing in FIG. 20 illustrates a reference X-ray spectrum that is detected by an X-ray detection element A serving as the reference detection element and has not been subjected to preprocessing. The spectrum processor 33c removes an offset to generate an X-ray spectrum as illustrated in the right drawing in FIG. 20. The spectrum processor 33c determines an upper limit value of the band of the X-ray spectrum as follows. For example, the spectrum processor 33c estimates the upper limit of the energy value based on the tube voltage of the X-ray tube 12 to remove an X-ray spectrum having an energy value that is equal to or higher than the estimated upper limit value. The spectrum processor 33c also determines a lower limit value of the band of the X-ray spectrum as follows. For example, the spectrum processor 33c removes an X-ray spectrum having an energy value that is less than or equal to the energy value removed by a bow tie filter that is not illustrated.

Thereafter, FIG. 21 illustrates smoothing processing. The left drawing in FIG. 21 illustrates a reference X-ray spectrum that is detected by an X-ray detection element A serving as the reference detection element and has not been subjected to preprocessing. The spectrum processor 33c removes noise of the X-ray spectrum illustrated in the left drawing in FIG. 21 to generate an X-ray spectrum with a stable average value as illustrated in the right drawing in FIG. 21.

Thereafter, the calculator 33a according to the third embodiment calculates the centroid of the preprocessed reference X-ray spectrum to calculate correction values for the respective X-ray detection elements. As described above, preprocessing the X-ray spectrum further reduces statistical errors.

The third embodiment illustrates the case of preprocessing a reference X-ray spectrum, but the embodiment is not limited thereto. For example, the spectrum processor 33c may preprocess a reference X-ray spectrum and an X-ray spectrum detected by the detector 13 of photon-counting type. In such a case, the calculator 33a calculates the centroid of the preprocessed reference X-ray spectrum and the centroid of the X-ray spectrum detected by the detector 13 of photon-counting type to calculate correction values for the respective X-ray detection elements. The spectrum processor 33c may preprocess only the X-ray spectrum detected by the detector 13 of photon-counting type, without preprocessing the reference X-ray spectrum.

Other Embodiments

Embodiments are not limited to the above embodiments.

The first to third embodiments described above illustrate that the charge amplifier 141 outputs a pulse signal to the calculator 33a of the scan controller 33 in the case of performing processing of calculating correction values, but the embodiments are not limited thereto. For example, the waveform shaping circuit 143 may output a pulse signal to the calculator 33a of the scan controller 33. In such a case, the waveform shaping circuit 143 switches output of a pulse signal to one of the scan controller 33 and the pulse shape discriminating circuit 144, in accordance with an instruction from the scan controller 33.

In addition, the first to third embodiments illustrate that the X-ray CT apparatus calculates correction values, but the embodiments are not limited thereto. For example, the image processing method described in the first to third embodiments may have a structure in which an image processing apparatus having a calculator with the same function as that of the calculator 33a calculates correction values. In such a case, the calculator of the image processing apparatus acquires detection signals detected by a calibrated spectrometer or reference detection elements from the X-ray CT apparatus. The calculator of the image processing apparatus calculates correction values to match centroids of X-ray spectrums detected by the respective X-ray detection elements with the centroid of a reference X-ray spectrum detected by the calibrated spectrometer or the reference detection elements.

The image processing apparatus may further include a spectrum processor having the same function as that of the spectrum processor 33c according to the third embodiment. In such a case, the calculator of the image processing apparatus calculates a centroid of a preprocessed reference X-ray spectrum, to calculate correction values for the respective X-ray detection elements.

The first to third embodiments illustrate the case of reconstructing an X-ray CT image by the X-ray CT apparatus, but the embodiments are not limited thereto. For example, an apparatus other than the X-ray CT apparatus may reconstruct an X-ray CT image, as long as the apparatus can acquire raw data collected by the X-ray CT apparatus. For example, the image processing apparatus corrects detection signals collected by the X-ray CT apparatus based on correction values for the respective X-ray detection elements, to reconstruct an X-ray CT image using the corrected detection signals.

Software may implement the functions of the waveform shaping circuit 143 and the image reconstruction unit 36 described in the first to third embodiments. For example, the functions of the waveform shaping circuit 143 and the image reconstruction unit 36 are implemented by causing a computer to execute an image processing program that provides the procedure of the processing performed by the waveform shaping circuit 143 and the image reconstruction unit 36 in the above embodiments. The image processing program is stored in, for example, a hard disk or a semiconductor memory device, to be read and executed by a processor such as a central processing unit (CPU) and a micro-processor unit (MPU). The image processing program may be stored and distributed in a computer-readable storage medium such as a compact-disc-read only memory (CD-ROM), a magnetic optical disk (MO), and a digital versatile disc (DVD). The image processing program may further cause a computer to execute the procedure of processing that is performed by the calculator 33a in the first to third embodiments. In the same manner, software may implement the functions of the movement controller 33b explained in the second embodiment and the functions of the spectrum processor 33c explained in the third embodiment.

At least one of the embodiments described above enables accurate and simple calibration.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray computed tomography (CT) apparatus comprising:
   a photon-counting detector configured to include a plurality of X-ray detection elements detecting X-ray photons applied from an X-ray tube;
   correction circuitry configured to correct detection signals detected by the photon-counting detector for the plurality of X-ray detection elements, based on a centroid of an X-ray spectrum detected by the photon-counting detector; and
   reconstruction circuitry configured to reconstruct a CT image based on the corrected detection signals.

2. The X-ray CT apparatus according to claim 1, further comprising:
   a calculator configured to calculate correction values, for the plurality of X-ray detection elements, to match a reference centroid serving as a centroid of a reference X-ray spectrum with the centroid of the X-ray spectrum detected by the photon-counting detector, wherein
   the correction circuitry corrects the detection signals detected by the photon-counting detector for the (plurality of X-ray detection elements, based on the correction values calculated for the plurality of X-ray detection elements.

3. The X-ray CT apparatus according to claim 2, wherein the calculator calculates the reference X-ray spectrum from a detection signal detected using a spectrometer, and determines the reference centroid from the reference X-ray spectrum, to calculate the correction values for the plurality of X-ray detection elements.

4. The X-ray CT apparatus according to claim 3, wherein
   the calculator calculates the correction values for the plurality of X-ray detection elements in accordance with a tube voltage of the X-ray tube, and
   the correction circuitry corrects the detection signals detected by the photon-counting detector for the plurality of X-ray detection elements, based on the correction values in accordance with the tube voltage of the X-ray tube.

5. The X-ray CT apparatus according to claim 2, further comprising:
   a reference detection element configured to have higher energy resolution than that of the plurality of X-ray detection elements included in the photon-counting detector, wherein
   the calculator determines the reference X-ray spectrum from a detection signal detected using the reference detection element, and determines the reference centroid based on characteristic X-rays of the reference X-ray spectrum, to calculate the correction values for the plurality of X-ray detection elements.

6. The X-ray CT apparatus according to claim 5, further comprising:
   a movement controller configured to control movement of the photon-counting detector in a channel direction independently of the X-ray tube, and perform control to match a position of the reference detection element in the channel direction when the reference centroid is determined with a position of an X-ray detection element of the plurality of X-ray detection elements that is to be corrected in the channel direction.

7. The X-ray CT apparatus according to claim 6, wherein the movement controller places the reference detection element in a position opposed to the X-ray tube when the reference centroid is determined, and places the X-ray detection element of the plurality of X-ray detection elements that is to be corrected in the position opposed to the X-ray tube.

8. The X-ray CT apparatus according to claim 6, wherein the movement controller places the reference detection element in a position agreeing with a relative position between the X-ray detection element of the plurality of X-ray detection elements that is to be corrected and the X-ray tube in a state where a center of the photon-counting detector is opposed to the X-ray tube when the reference centroid is determined, and places the center of the photon-counting detector in the position opposed to the X-ray tube.

9. The X-ray CT apparatus according to claim 5, wherein the photon-counting detector includes the reference detection element in at least part of the plurality of X-ray detection elements.

10. The X-ray CT apparatus according to claim 2, further comprising:
    a spectrum processor configured to preprocess the reference X-ray spectrum, wherein
    the calculator calculates the reference centroid from the preprocessed reference X-ray spectrum, to calculate the correction values for the plurality of X-ray detection elements.

11. The X-ray CT apparatus according to claim 1, wherein the photon-counting detector is an area detector.

12. The X-ray CT apparatus according to claim 1, wherein the centroid of the X-ray spectrum is an energy position in which an area of X-ray spectrum in an energy band higher than the centroid is equal to an area of X-ray spectrum in an energy band lower than the centroid.

13. An image processing apparatus, comprising:

correction circuitry configured to correct detection signals detected by a photon-counting detector including a plurality of X-ray detection elements configured to detect X-ray photons applied from an X-ray tube, for the plurality of X-ray detection elements, based on a centroid of an X-ray spectrum detected by the photon-counting detector; and reconstruction circuitry configured to reconstruct a computed tomography (CT) image based on the corrected detection signals.

14. An image processing method comprising:

correcting detection signals detected by a photon-counting detector including a plurality of X-ray detection elements configured to detect X-ray photons applied from an X-ray tube, for the plurality of X-ray detection elements, based on a centroid of an X-ray spectrum detected by the photon-counting detector; and reconstructing a computed tomography (CT) image based on the corrected detection signals.

* * * * *